(12) United States Patent
Nagaoka et al.

(10) Patent No.: US 9,871,210 B2
(45) Date of Patent: Jan. 16, 2018

(54) NAPHTHOTRIAZOLE DERIVATIVES AND ORGANIC ELECTROLUMINESCENCE DEVICES

(71) Applicant: HODOGAYA CHEMICAL CO., LTD., Tokyo (JP)

(72) Inventors: Makoto Nagaoka, Tokyo (JP); Shigetaka Numazawa, Tokyo (JP); Mari Toriya, Tokyo (JP); Shingo Ozawa, Tokyo (JP); Shigeru Kusano, Tokyo (JP)

(73) Assignee: HODOGAYA CHEMICAL CO., LTD., Tokyo (JP)

( * ) Notice: Subject to any disclaimer, the term of this patent is extended or adjusted under 35 U.S.C. 154(b) by 130 days.

(21) Appl. No.: 14/769,651

(22) PCT Filed: Feb. 20, 2014

(86) PCT No.: PCT/JP2014/053995
§ 371 (c)(1),
(2) Date: Aug. 21, 2015

(87) PCT Pub. No.: WO2014/132871
PCT Pub. Date: Sep. 4, 2014

(65) Prior Publication Data
US 2016/0005982 A1 Jan. 7, 2016

(30) Foreign Application Priority Data
Feb. 26, 2013 (JP) ................................ 2013-035979

(51) Int. Cl.
*H01L 51/00* (2006.01)
*C07D 401/04* (2006.01)
(Continued)

(52) U.S. Cl.
CPC ........ *H01L 51/0072* (2013.01); *C07D 401/04* (2013.01); *C07D 401/10* (2013.01);
(Continued)

(58) Field of Classification Search
None
See application file for complete search history.

(56) References Cited

U.S. PATENT DOCUMENTS 5,869,199 A 2/1999 Kido
6,878,469 B2 4/2005 Yoon et al.
(Continued)

FOREIGN PATENT DOCUMENTS

JP 2734341 3/1998
JP 2005-529172 9/2005
(Continued)

OTHER PUBLICATIONS

International Search Report issued in Patent Application No. PCT/JP2014/053995, dated Apr. 15, 2014.

*Primary Examiner* — J. L. Yang
(74) *Attorney, Agent, or Firm* — Greenblum & Bernstein, P.L.C.

(57) ABSTRACT

Naphthotriazole derivatives represented by the following general formula (1), (Continued)

9 CATHODE
8 ELECTRON INJECTION LAYER
7 ELECTRON-TRANSPORTING LAYER
6 HOLE-BLOCKING LAYER
5 LUMINOUS LAYER
4 HOLE-TRANSPORTING LAYER
3 HOLE INJECTION LAYER
2 TRANSPARENT ANODE
1 GLASS SUBSTRATE

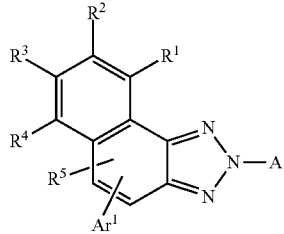

(1)

wherein, Ar¹ is an aromatic hydrocarbon group or an aromatic heterocyclic group, and A is a group that contains an aromatic heterocyclic group. The compound features excellent electron injection/transporting capability, a high hole-blocking power and a high stability in the form of a thin film, and can be used as a material for producing highly efficient and highly durable organic electroluminescent devices.

13 Claims, 5 Drawing Sheets

(51) Int. Cl.
| C07D 401/10 | (2006.01) |
| C07D 409/14 | (2006.01) |
| C09K 11/06 | (2006.01) |
| C07D 401/14 | (2006.01) |
| H01L 51/50 | (2006.01) |

(52) U.S. Cl.
CPC ......... *C07D 401/14* (2013.01); *C07D 409/14* (2013.01); *C09K 11/06* (2013.01); *H01L 51/0052* (2013.01); *H01L 51/0067* (2013.01); *H01L 51/0074* (2013.01); *C09K 2211/1007* (2013.01); *C09K 2211/1011* (2013.01); *C09K 2211/1029* (2013.01); *C09K 2211/1059* (2013.01); *C09K 2211/1092* (2013.01); *H01L 51/0058* (2013.01); *H01L 51/5012* (2013.01); *H01L 51/5072* (2013.01); *H01L 51/5092* (2013.01); *H01L 51/5096* (2013.01)

(56) References Cited

U.S. PATENT DOCUMENTS

| 2005/0175856 A1 | 8/2005 | Rogers et al. |
| 2007/0043204 A1 | 2/2007 | Rogers et al. |
| 2008/0027226 A1 | 1/2008 | Rogers et al. |
| 2009/0066231 A1 | 3/2009 | Oka et al. |
| 2012/0012831 A1 | 1/2012 | Yokoyama et al. |

FOREIGN PATENT DOCUMENTS

| JP | 2006-526671 | 11/2006 |
| JP | 2007-518705 | 7/2007 |
| JP | 2008-539192 | 11/2008 |
| WO | 03/060956 | 7/2003 |
| WO | 2010/107074 | 9/2010 |

9  CATHODE
8  ELECTRON INJECTION LAYER
7  ELECTRON-TRANSPORTING LAYER
6  HOLE-BLOCKING LAYER
5  LUMINOUS LAYER
4  HOLE-TRANSPORTING LAYER
3  HOLE INJECTION LAYER
2  TRANSPARENT ANODE
1  GLASS SUBSTRATE

NAPHTHOTRIAZOLE DERIVATIVES AND ORGANIC ELECTROLUMINESCENCE DEVICES

FIELD OF THE INVENTION

This invention relates to novel naphthotriazole derivatives. More specifically, the invention relates to novel naphthotriazole derivatives into which a naphthotriazole ring structure has been introduced and to organic electroluminescent devices that have an organic layer containing the above derivatives between the electrodes.

BACKGROUND ART

An organic electroluminescent device (hereinafter often called organic EL device) is a spontaneously luminous device which features higher brightness and higher legibility than those of the liquid crystal devices enabling vivid display to be attained and has, therefore, been vigorously studied.

In 1987, C. W. Tang et al. of the Eastman Kodak Co. have developed a device of a layer-laminated structure comprising various kinds of materials to bear individual roles, and have put an organic EL device using organic materials into a practical use. The above organic EL device is constituted by laminating layers of a fluorescent body capable of transporting electrons and an organic material capable of transporting holes. Upon injecting both electric charges into the layer of the fluorescent body to emit light, the device is capable of attaining a brightness of as high as 1000 cd/m$^2$ or more with a voltage of not higher than 10 V.

So far, very many improvements have been made to put the organic EL device to practical use. For example, the organic EL device has been widely known having a structure comprising an anode, a hole injection layer, a hole-transporting layer, a luminous layer, an electron-transporting layer, an electron injection layer and a cathode which are arranged in this order on a substrate more finely dividing their roles than ever before. The device of this kind is achieving a high efficiency and a high durability.

To further improve the luminous efficiency, attempts have been made to utilize triplet excitons and study has been forwarded to utilize a phosphorescent luminous compound.

In the organic EL device, the electric charges injected from the two electrodes recombine together in the luminous layer to emit light. Here, however, the hole migration rate is higher than the electron migration rate arousing a problem of a decrease in the efficiency since the holes partly pass through the luminous layer. Therefore, it has been desired to provide an electron-transporting material that has a higher electron migration rate.

Tris(8-hydroxyquinoline)aluminum (hereinafter abbreviated as Alq$_3$) which is a representative luminous material has also been generally used as an electron-transporting material having, however, a low electron mobility and a work function of 5.6 eV and, therefore, having a hole-blocking capability which is far from satisfactory.

A method of inserting a hole-blocking layer is one of the measures for preventing the holes from partly passing through the luminous layer to improve the probability of recombination of the electric charge in the luminous layer.

As a hole-blocking material used for forming the hole-blocking layer, for example, a patent document 1 discloses a 3-(4-biphenylyl)-4-phenyl-5-(4-t-butylphenyl)-1,2,4-triazole (hereinafter abbreviated as TAZ).

As the hole-blocking material, there have, further, been known a bathocuproin (hereinafter abbreviated as BCP) and a mixed ligand complex of aluminum such as aluminum (III) bis(2-methyl-8-quinolinato)-4-phenyl phenolate (hereinafter abbreviated as BAlq).

The TAZ has a work function of as large as 6.6 eV and a large hole-blocking power, and is used for forming an electron-transporting hole-blocking layer that is laminated on the cathode side of a fluorescent luminous layer or a phosphorescent luminous layer prepared by vacuum evaporation or by coating and, therefore, contributes to improving the efficiency of the organic EL devices.

Because of its low electron-transporting capability, however, the TAZ had to be used in combination with an electron-transporting material having a higher electron-transporting capability. The BCP, on the other hand, has a work function of as large as 6.7 eV and a large hole-blocking power but a glass transition point (Tg) of as low as 83° C. In the form of a thin film, therefore, the BCP lacks stability and still leaves much room for improvement for forming a hole-blocking layer that works maintaining stability.

A patent document 2 discloses a general electron-transporting compound which, however, still lacks stability when it is formed into a film or lacks the function for blocking the holes to a sufficient degree.

In order to improve characteristics of the organic electroluminescent devices, therefore, it has been desired to provide an organic compound that excels in electron injection/transporting capability and in hole-blocking power, and features high stability in the form of a thin film.

PRIOR ART DOCUMENTS

Patent Documents

Patent document 1: Japanese Patent No. 2734341
Patent document 2: WO2003/060956

OUTLINE OF THE INVENTION

Problems that the Invention is to Solve

The object of the present invention is to provide a novel organic compound that excels in electron injection/transporting capability, features a high hole-blocking power and a high stability in the form of a thin film, and can be used as a material for producing highly efficient and highly durable organic electroluminescent devices.

Another object of the invention is to provide a highly efficient and highly durable organic electroluminescent device having an organic layer that is formed by using the above organic compound.

Means for Solving the Problems

To achieve the above objects, the present inventors have paid attention to that a hetero atom of an aromatic heterocyclic ring having affinity to electron has a capability of being coordinated on a metal, that a naphthotriazole ring structure has a high electron transporting capability, that the aromatic heterocyclic ring and, specifically, the naphthotriazole ring structure has excellent resistance against the heat, and have designed and chemically synthesized a compound that has the naphthotriazole ring structure, have prepared various organic electroluminescent devices by using the above compound on an experimental basis, have keenly evaluated the properties of the device and, as a result, have confirmed that a high efficiency and a high durability can be obtained and have thus completed the present invention.

According to the present invention, there are provided Naphthotriazole derivatives represented by the following general formula (1),

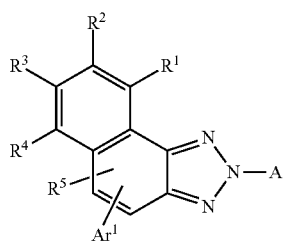

(1)

wherein,
Ar¹ is an aromatic hydrocarbon group or an aromatic heterocyclic group,
R¹ to R⁵ may be the same or different, and are hydrogen atoms, deuterium atoms, fluorine atoms, chlorine atoms, cyano groups, alkyl groups having 1 to 6 carbon atoms, aromatic hydrocarbon groups or aromatic heterocyclic groups,
A is a monovalent group represented by the following structural formula (1a),

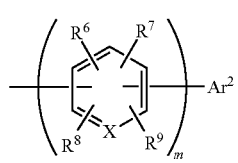

(1a)

wherein,
m is an integer of 0, 1 or 2,
Ar² is an aromatic heterocyclic group,
R⁶ to R⁹ may be the same or different, and are hydrogen atoms, deuterium atoms, fluorine atoms, chlorine atoms, cyano groups, alkyl groups having 1 to 6 carbon atoms, aromatic hydrocarbon groups or aromatic heterocyclic groups,
X is a carbon atom or a nitrogen atom, and
wherein if X is a nitrogen atom, R⁹ is not present on the ring that includes the nitrogen atoms, if m is 0, Ar² is directly bonded to the nitrogen atom in the triazole ring and if m is 2, the plurality of R⁶ to R⁹ and X may be the same or different from each other.

According to the present invention, further, there is provided an organic electroluminescent device having a pair of electrodes and at least one organic layer interposed therebetween, wherein at least one of the organic layers contains the naphthotriazole derivative.

In the organic EL device of the invention, the organic layer containing the naphthotriazole derivative is, for example, an electron-transporting layer, a hole-blocking layer, a luminous layer or an electron injection layer.

Effects of the Invention

The naphthotriazole derivatives of the invention represented by the above general formula (1) are novel compounds and have a naphthotriazole ring and an aromatic heterocyclic ring. The naphthotriazole derivatives having the above structure feature the following properties.
(A) The electrons can be favorably injected.
(B) The electrons migrate at a high rate.
(C) The holes can be blocked favorably.
(D) Remains stable in a thin-film state.
(E) Excellent heat resistance.

Owing to their stability in their thin-film state, the naphthotriazole derivatives of the present invention can be used as an organic layer that is provided between the electrodes of an organic electroluminescent device, and impart the following properties to the organic EL device.
(F) A high luminous efficiency and a high power efficiency.
(G) A low luminescence start voltage.
(H) A low practical driving voltage.
(I) A long service life of the device (large durability).

For instance, the organic EL device forming the electron injection layer and/or the electron-transporting layer by using the naphthotriazole derivative of the invention, features a high electron injection/migration rate, an improved electron transport efficiency from the electron-transporting layer into the luminous layer and, therefore, features a high luminous efficiency, a low driving voltage and a large durability.

Further, the organic EL device having a hole-blocking layer formed by using the naphthotriazole derivative of the invention features excellent hole-blocking power and electron-transporting capability and, therefore, requires a decreased driving voltage yet maintaining a high luminous efficiency and, besides, features an improved resistance against the electric current and an improved maximum brightness.

Further, the naphthotriazole derivative of the invention features excellent electron transport capability and a wide band gap and can, therefore, be used as a host material for the luminous layer. By using the naphthotriazole derivative of the invention as a luminous layer which, further, carries a fluorescent material or a luminous phosphor called dopant thereon, it is made possible to lower the driving voltage of the organic EL device and to improve the luminous efficiency.

As described above, the naphthotriazole derivative of the present invention is useful as a material for constituting the electron injection layer, electron-transporting layer, hole-blocking layer or luminous layer of the organic EL device, works to improve the luminous efficiency and the power efficiency of the organic EL device, to lower the practical driving voltage, to realize a low luminescence start voltage and to increase the durability.

MODES FOR CARRYING OUT THE INVENTION

Figure 1:
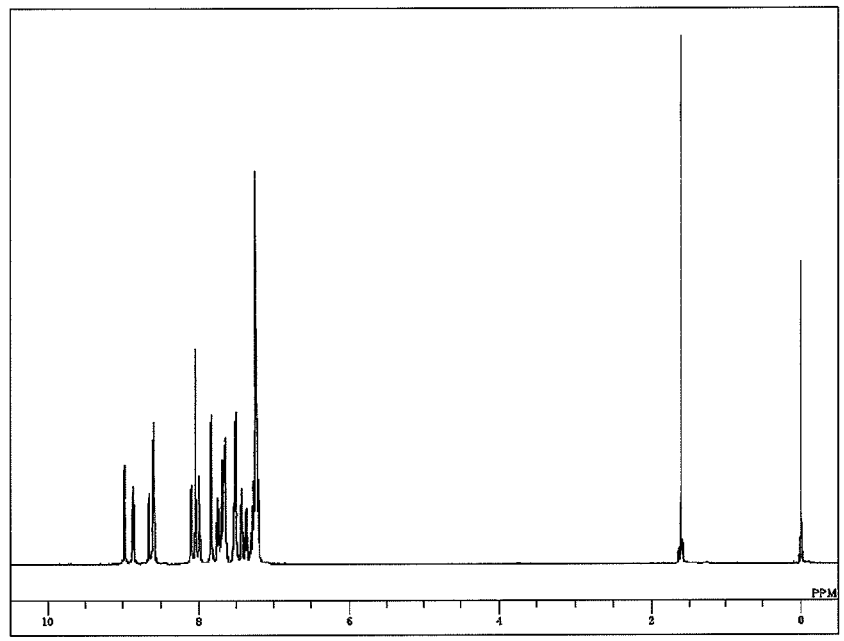
FIG. 1: ¹H-NMR chart of compound (compound 9) of Example 1.

The novel naphthotriazole derivatives of the present invention are represented by the following formula (1) and have a structure in which an aromatic heterocyclic group Ar² is bonded to a nitrogen atom in the napthotriazole ring directly or via a divalent group,

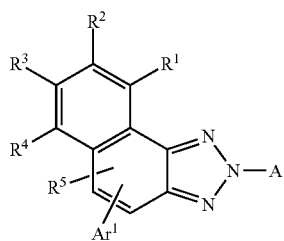

(1)

<Group Ar¹>

In the above general formula (1), Ar¹ is an aromatic hydrocarbon group or an aromatic heterocyclic group. The aromatic hydrocarbon group and the aromatic heterocyclic group may have a monocyclic structure or a condensed polycyclic structure.

Examples of these aromatic groups (aromatic hydrocarbon groups and aromatic heterocyclic groups) include phenyl group, biphenylyl group, terphenylyl group, tetrakisphenyl group, styryl group, naphthyl group, anthryl group, acenaphthenyl group, phenanthryl group, fluorenyl group, indenyl group, pyrenyl group, triazyl group, pyridyl group, pyrimidyl group, furyl group, pyrolyl group, thienyl group, quinolyl group, isoquinolyl group, benzofuranyl group, benzothienyl group, indolyl group, carbazolyl group, benzoxazolyl group, benzothiazolyl group, quinoxalyl group, benzimidazolyl group, pyrazolyl group, dibenzofuranyl group, dibenzothienyl group, naphthyridinyl group, phenanthrolinyl group and acridinyl group.

The above aromatic groups may have a substituent.

As the substituent, there can be exemplified deuterium atom; fluorine atom; chlorine atom; cyano group; trifluoromethyl group; hydroxyl group; nitro group; straight-chain or branched alkyl group having 1 to 6 carbon atoms; cyclic alkyl group (e.g., cyclopentyl group, cyclohexyl group); straight-chain or branched alkoxy group having 1 to 6 carbon atoms; dialkyl-substituted group having, as a substituent, a straight-chain or branched alkyl group having 1 to 6 carbon atoms; aryl groups such as phenyl group, naphthyl group, anthryl group, fluorenyl group and styryl group; and aromatic heterocyclic groups such as pyridyl group, pyridoindolyl group, quinolyl group, isoquinolyl group and benzothiazolyl group. These substituents may, further, have substituents that are exemplified above.

The alkyl groups and alkoxy groups in the above substituents may be the same as those represented by R¹ to R⁵ in the general formula (1) that will be described below.

<Groups R¹ to R⁵>

In the general formula (1), R¹ to R⁵ may be the same or different and are hydrogen atoms, deuterium atoms fluorine atoms, chlorine atoms, cyano groups, alkyl groups having 1 to 6 carbon atoms, aromatic hydrocarbon groups or aromatic heterocyclic groups.

The alkyl groups having 1 to 6 carbon atoms may be in the form of a straight chain or may be branched, and are methyl groups, ethyl groups, n-propyl groups, i-propyl groups, n-butyl groups, 2-methylpropyl groups, t-butyl groups, n-pentyl groups, 3-methylbutyl groups, tert-pentyl groups, n-hexyl groups, iso-hexyl groups or tert-hexyl groups.

The aromatic hydrocarbon groups and aromatic heterocyclic groups may have a monocyclic structure or a condensed polycyclic structure. Besides, these aromatic groups may be the same as the aromatic groups represented by Ar¹.

Further, the aromatic hydrocarbon groups and the aromatic heterocyclic groups may have a substituent. As the substituent, there can be exemplified those that may be possessed by the aromatic group Ar¹.

<Group A>

In the general formula (1), the monovalent group A bonded to the nitrogen atom in the naphthotriazole ring is a group that contains an aromatic heterocyclic group (Ar²), and is concretely represented by the following structural formula (1a),

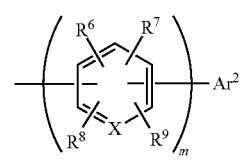

(1a)

In the above structural formula (1a), m is an integer of 0, 1 or 2.

Further, Ar² is an aromatic heterocyclic group, R⁶ to R⁹ are hydrogen atoms, deuterium atoms, fluorine atoms, chlorine atoms, cyano groups, alkyl groups having 1 to 6 carbon atoms, aromatic hydrocarbon groups or aromatic heterocyclic groups.

Further, X is a carbon atom or a nitrogen atom, and if X is a nitrogen atom, R⁹ is not present on the ring that includes the nitrogen atoms, if m is 0, Ar² is directly bonded to the nitrogen atom in the triazole ring and if m is 2, the plurality of R⁶ to R⁹ and X may be the same or different from each other.

In the above structural formula (1a), examples of the aromatic heterocyclic group represented by Ar² include such groups as triazinyl group, pyridyl group, pyrimidyl group, furyl group, pyrrolyl group, thienyl group, quinolyl group, isoquinolyl group, benzofuranyl group, benzothienyl group, indolyl group, carbazolyl group, benzoxazolyl group, benzothiazolyl group, quinoxalyl group, benzimidazolyl group and pyrazolyl group.

Among them, preferred examples are the nitrogen-containing aromatic heterocyclic groups such as triazinyl group, pyridyl group, pyrimidyl group, quinolyl group, isoquinolyl group, indolyl group, carbazolyl group, benzoxazolyl group, benzothiazolyl group, quinoxalyl group, benzimidazolyl group and pyrazolyl group. More preferred examples are pyridyl group, quinolyl group and isoquinolyl group, and most preferred example is the pyridyl group.

Further, the aromatic heterocyclic group represented by Ar² may have a substituent. Concretely, there can be exemplified the same substituents as those that may be possessed by Ar¹ in the general formula (1).

As described above, further, if m is 0, $Ar^2$ (aromatic heterocyclic group) is directly bonded to the nitrogen atom in the triazole ring.

The alkyl groups having 1 to 6 carbon atoms represented by $R^6$ to $R^9$ in the structural formula (1a) may be in the form of a straight chain or may be branched, and their concrete examples are the same as the alkyl groups represented by $R^1$ to $R^5$ in the general formula (1).

The aromatic hydrocarbon groups and the aromatic heterocyclic groups represented by $R^6$ to $R^9$ in the structural formula (1a) may have a monocyclic structure or a condensed polycyclic structure.

As the aromatic groups, there can be exemplified the same aromatic groups as those represented by $Ar^1$ in the general formula (1).

Further, the aromatic groups (aromatic hydrocarbon groups and aromatic heterocyclic groups represented by $R^6$ to $R^9$ may have a substituent. As the substituent, there can be exemplified the same substituents as those that may be possessed by $Ar^1$ in the general formula (1).

The naphthotriazole derivatives of the present invention represented by the above general formula (1) can be synthesized, for example, by a method described below.

First, an aminoarylazonaphthalene derivative is synthesized from a 1,2-diaminonaphthalene derivative and an aromatic heterocyclic derivative having a nitro group according to a known method.

The aminoarylazonaphthalene derivative is subjected to an oxidative cyclization reaction with an iodobenzenediacetate to synthesize a 2-arylnaphthotriazole derivative (e.g., see Aust. J. Chem., 45, 371 (1992)).

The thus obtained 2-arylnaphthotriazole derivative and various arylboron acid derivatives are subjected to a cross-coupling reaction such as Suzuki coupling to synthesize the naphthotriazole derivative of the present invention represented by the general formula (1).

The obtained compound is refined by a column chromatography, by an adsorption refining using silica gel, activated carbon or activated clay, by a recrystallization method using a solvent or by a crystallization method. The compound is identified by the NMR analysis.

Among the naphthotriazole derivatives of the present invention, many of favorable examples are those of the type in which $Ar^1$ in the general formula (1) is bonded to the fifth position of the naphthotriazole ring (fourth position of the naphthalene ring in the naphthotriazole ring), and are represented, for example, by the following general formula (1-1),

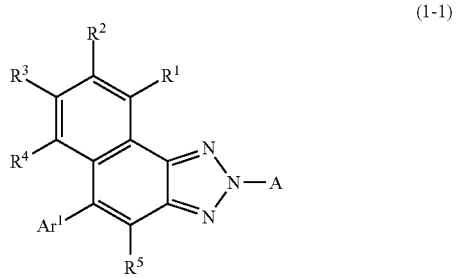

(1-1)

In the above general formula (1-1), $Ar^1$, $R^1$ to $R^5$ and a monovalent group A are, respectively as defined in the general formula (1).

In the invention, further, among those of the above general formula (1), preferred examples are the naphthotriazole derivatives having A that is represented by the following structural formula (A-1), (A-2) or (A-3).

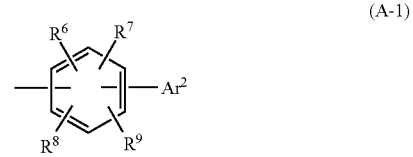

(A-1)

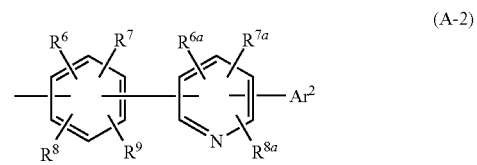

(A-2)

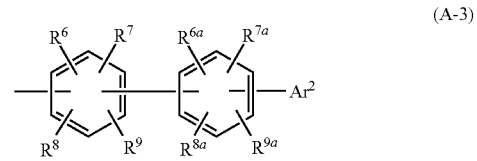

(A-3)

In the above general formulas (A-1), (A-2) and (A-3), $Ar^2$ and $R^6$ to $R^9$ are, respectively, as defined in the structural formula (1a).

That is, the above structural formula (A-1) is the one in which m of the group A represented by the structural formula (1a) is 1. The benzotriazole derivative having the group A represented by this structural formula has the aromatic heterocyclic group $Ar^2$ that is bonded to the nitrogen atom in the naphthotriazole ring via a benzene ring (X=C).

The structural formula (A-2) is the one in which m in the structural formula (1a) is 2. The benzotriazole derivative having the group A represented by this structural formula has the aromatic heterocyclic group $Ar^2$ that is bonded to the nitrogen atom in the naphthotriazole ring via a benzene ring (X=C) and a pyridine ring (X=N).

Further, the structural formula (A-3), too, is the one in which m in the structural formula (1a) is 2. In this case, however, the benzotriazole derivative having the group A represented by this structural formula has the aromatic heterocyclic group $Ar^2$ that is bonded to the nitrogen atom in the naphthotriazole ring via two benzene rings (X=C).

In the invention, the most desired naphthotriazole derivative has A represented by the following structural formula (A-4), (A-5), (A-6) or (A-7) in the above general formula (1).

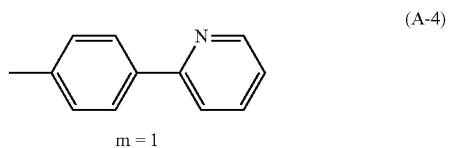

(A-4)

m = 1

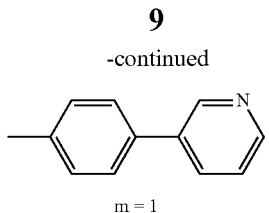

(A-5)

m = 1

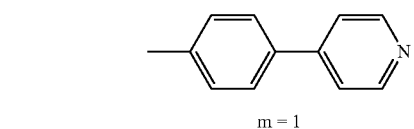

(A-6)

m = 1

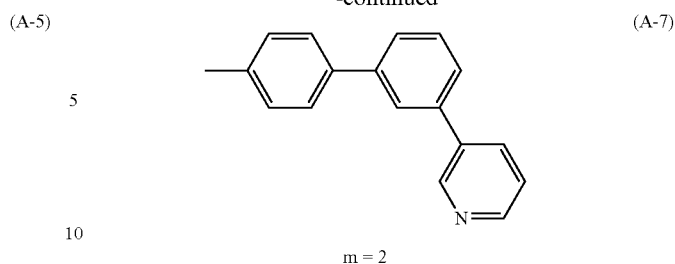

(A-7)

m = 2

Described below are concrete examples of the naphtho-triazole derivatives of the present invention to which only, however, the invention is in no way limited.

The following concrete examples show the values of m and kinds of X in the structural formula (1a) that represents the group A, as well as the numbers of the formulas representing the derivatives and the numbers of the formulas representing the groups A.

(Compound 1)

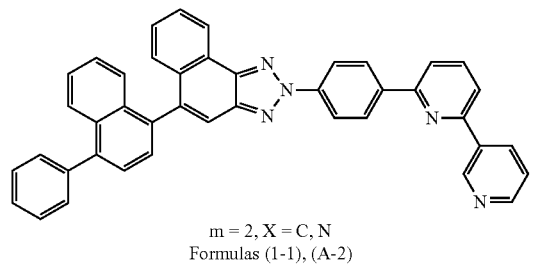

m = 2, X = C, N
Formulas (1-1), (A-2)

(Compound 2)

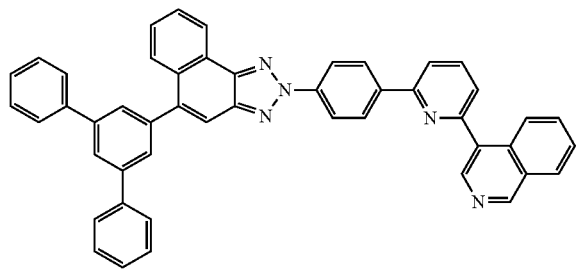

m = 2, X = C, N
Formulas (1-1), (A-2)

(Compound 3)

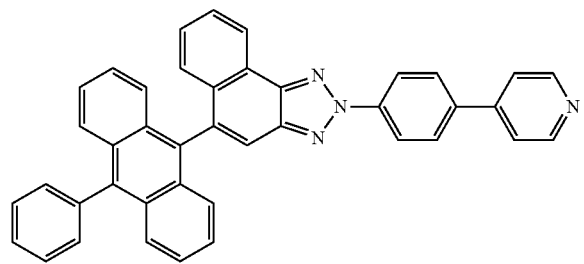

m = 1, X = C
Formulas (1-1), (A-1)

(Compound 4)

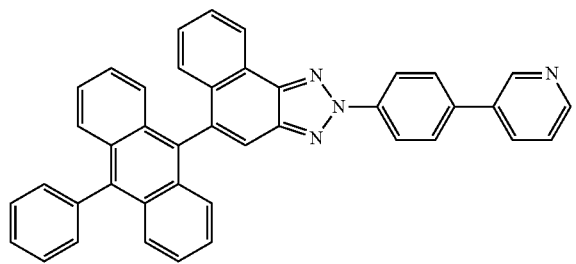

m = 1, X = C
Formulas (1-1), (A-1), (A-5)

-continued
(Compound 5)
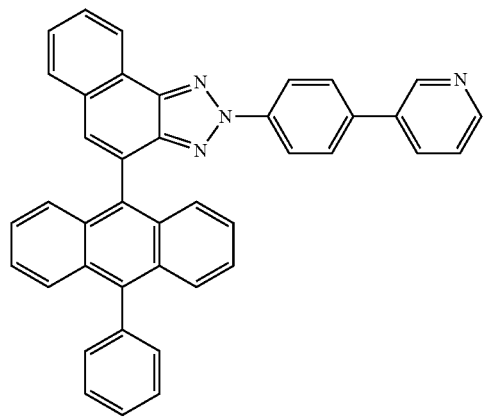
m = 1, X = C
Formulas (1), (A-1), (A-5)
(Compound 6)
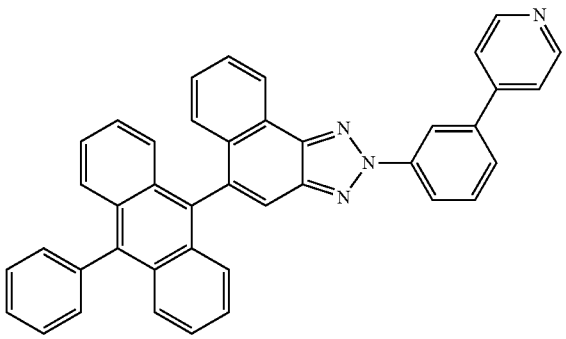
m = 1, X = C
Formulas (1-1), (A-1)
(Compound 7)
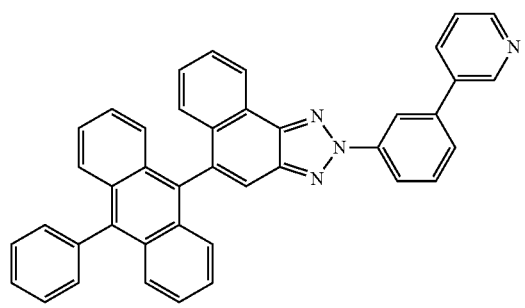
m = 1, X = C
Formulas (1-1), (A-1)
(Compound 8)
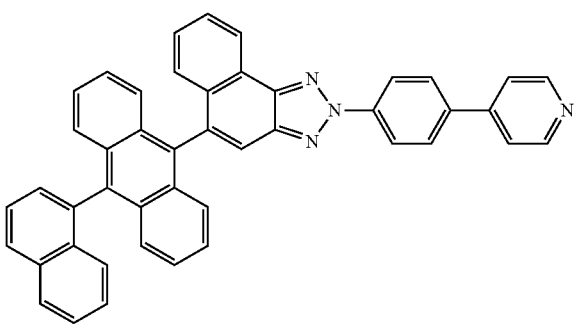
m = 1, X = C
Formulas (1-1), (A-1), (A-5)
(Compound 9)
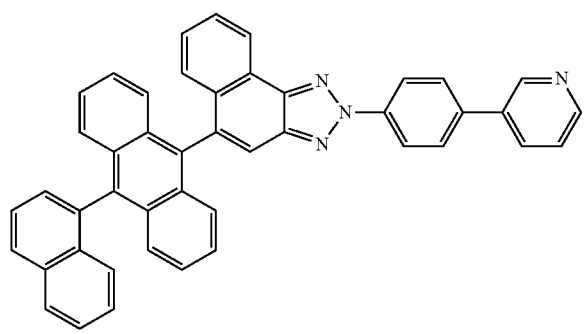
m = 1, X = C
Formulas (1-1), (A-1), (A-5)
(Compound 10)
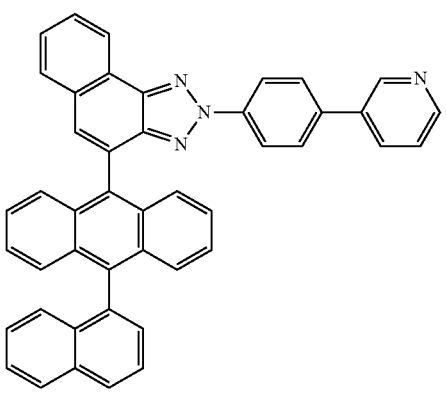
m = 1, X = C
Formulas (1), (A-1), (A-5)

-continued
(Compound 11)
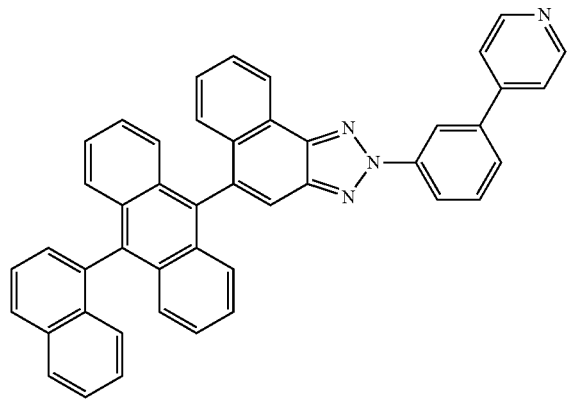
m = 1, X = C
Formulas (1-1), (A-1)
(Compound 12)
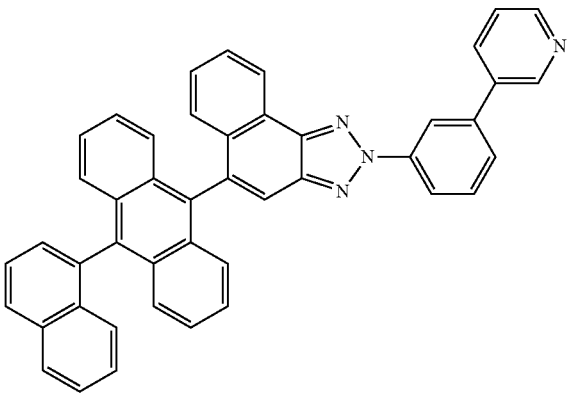
m = 1, X = C
Formulas (1-1), (A-1)
(Compound 13)
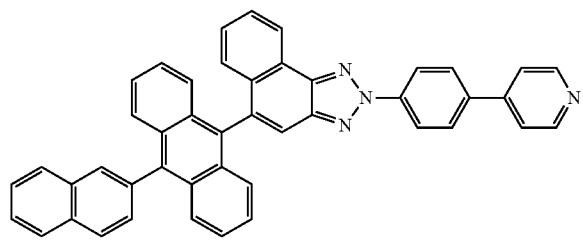
m = 1, X = C
Formulas (1-1), (A-1), (A-6)
(Compound 14)
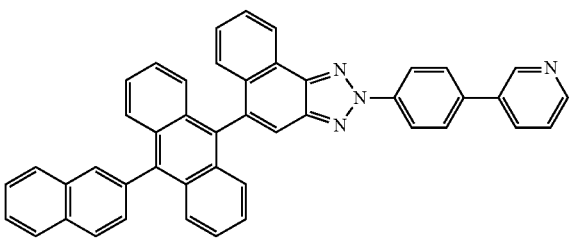
m = 1, X = C
Formulas (1-1), (A-1), (A-5)
(Compound 15)
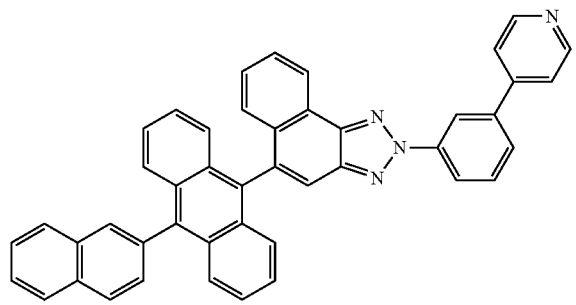
m = 1, X = C
Formulas (1-1), (A-1)
(Compound 16)
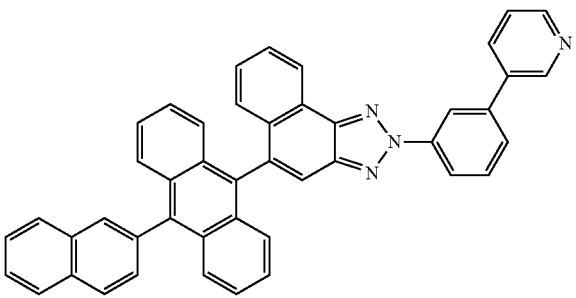
m = 1, X = C
Formulas (1-1), (A-1)
(Compound 17)
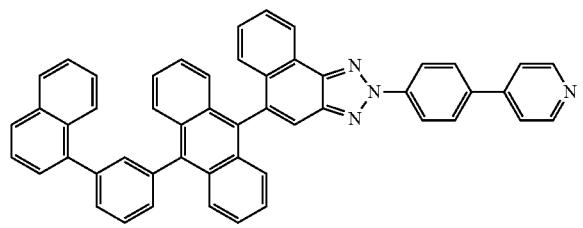
m = 1, X = C
Formulas (1-1), (A-1), (A-6)
(Compound 18)
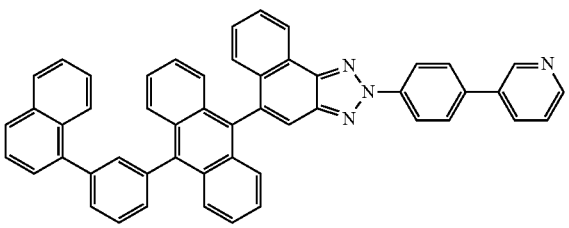
m = 1, X = C
Formulas (1-1), (A-1), (A-5)

-continued
(Compound 19)
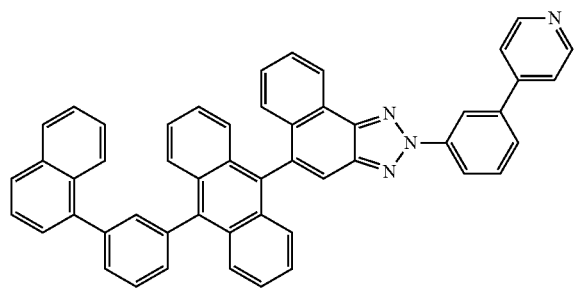
m = 1, X = C
Formulas (1-1), (A-1)
(Compound 20)
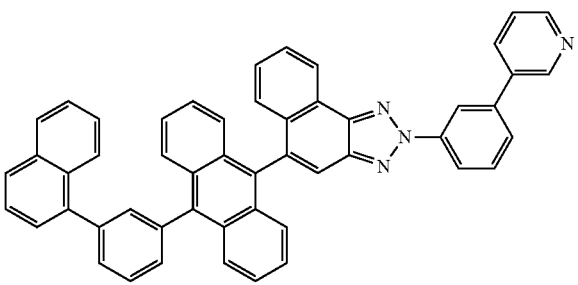
m = 1, X = C
Formulas (1-1), (A-1)
(Compound 21)
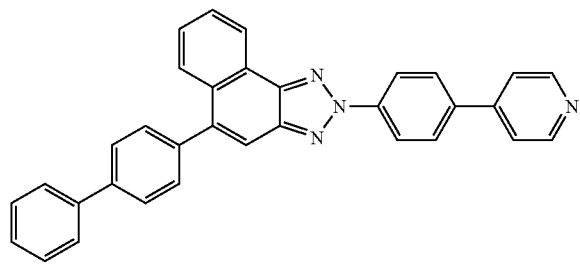
m = 1, X = C
Formulas (1-1), (A-1), (A-6)
(Compound 22)
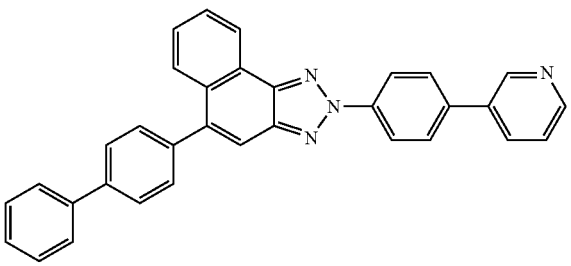
m = 1, X = C
Formulas (1-1), (A-1), (A-5)
(Compound 23)
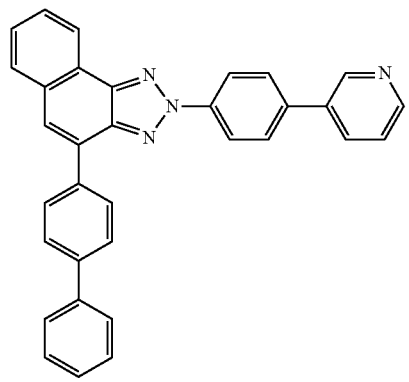
m = 1, X = C
Formulas (1), (A-1), (A-5)
(Compound 24)
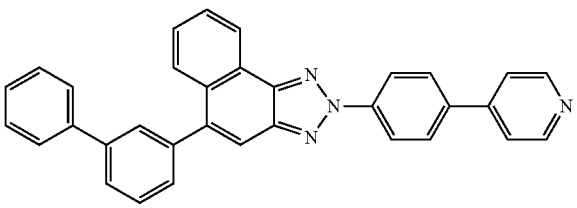
m = 1, X = C
Formulas (1-1), (A-1), (A-6)
(Compound 25)
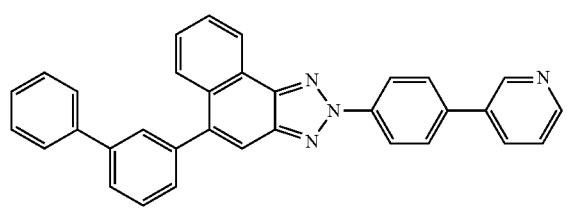
m = 1, X = C
Formulas (1-1), (A-1), (A-5)
(Compound 26)
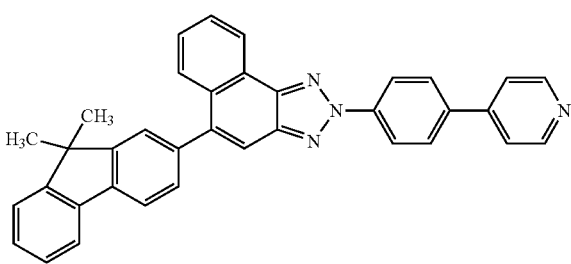
m = 1, X = C
Formulas (1-1), (A-1), (A-6)

-continued
(Compound 27)
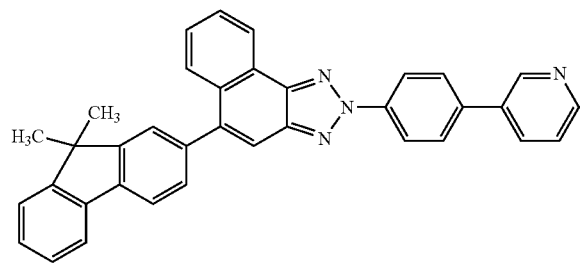
m = 1, X = C
Formulas (1-1), (A-1), (A-5)
(Compound 28)
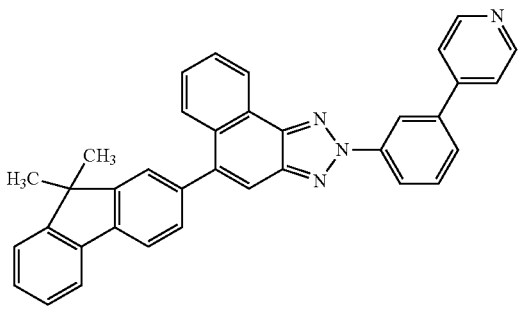
m = 1, X = C
Formulas (1-1), (A-1)
(Compound 29)
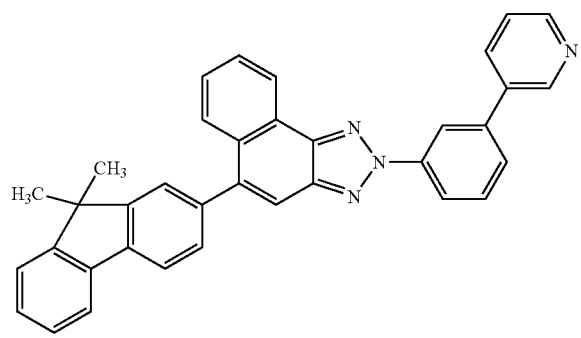
m = 1, X = C
Formulas (1-1), (A-1)
(Compound 30)
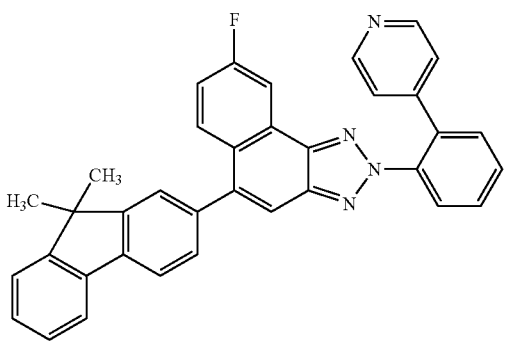
m = 1, X = C
Formulas (1-1), (A-1)
(Compound 31)
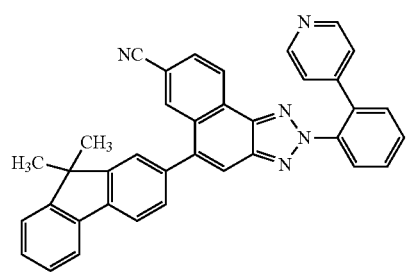
m = 1, X = C
Formulas (1-1), (A-1)
(Compound 32)
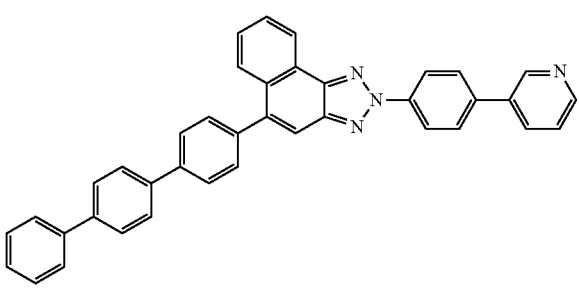
m = 1, X = C
Formulas (1-1), (A-1), (A-5)
(Compound 33)
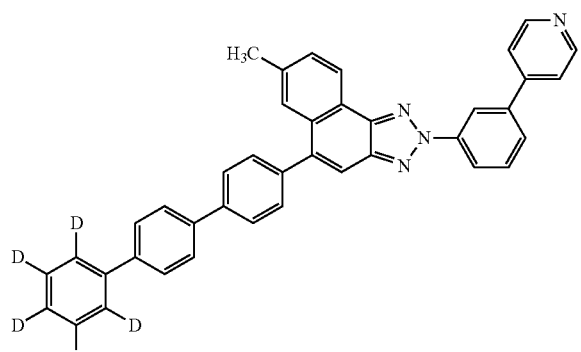
m = 1, X = C
Formulas (1-1), (A-1)
(Compound 34)
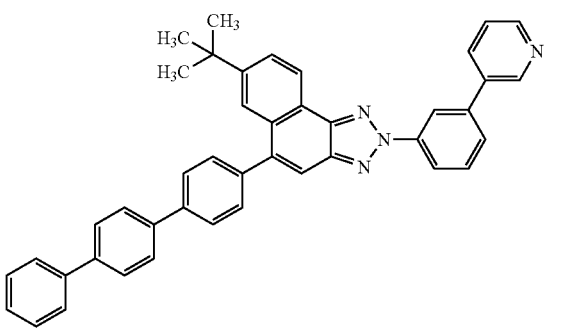
m = 1, X = C
Formulas (1-1), (A-1)

-continued
(Compound 35)
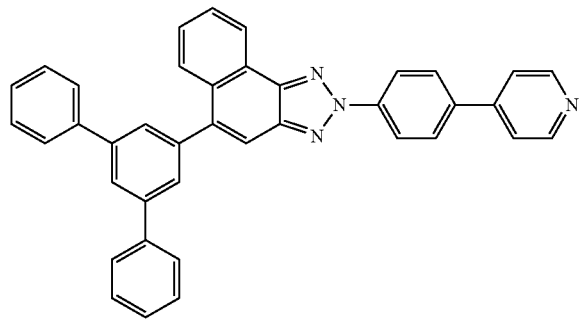
m = 1, X = C
Formulas (1-1), (A-1), (A-6)
(Compound 36)
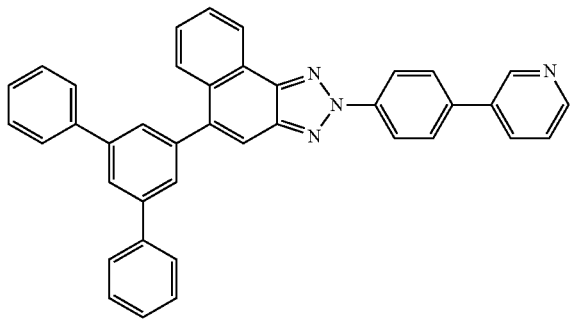
m = 1, X = C
Formulas (1-1), (A-1), (A-5)
(Compound 37)
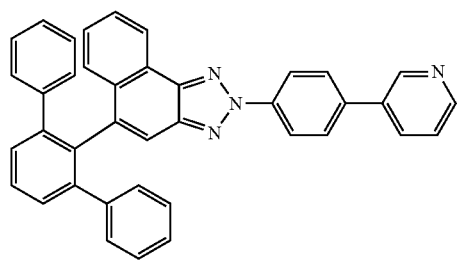
m = 1, X = C
Formulas (1-1), (A-1), (A-5)
(Compound 38)
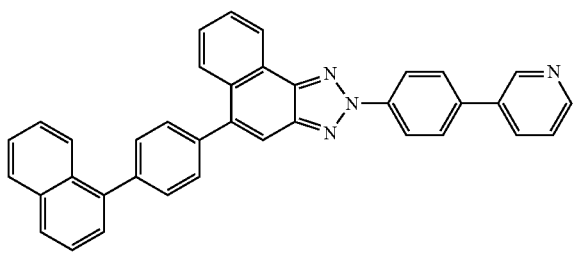
m = 1, X = C
Formulas (1-1), (A-1), (A-5)
(Compound 39)
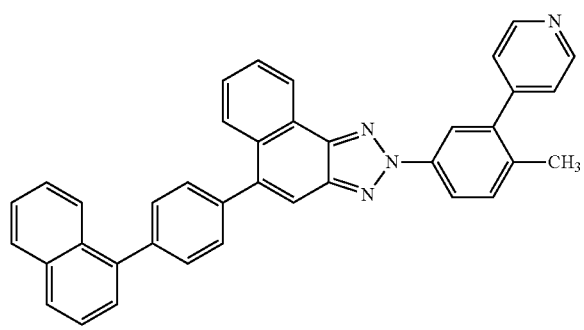
m = 1, X = C
Formulas (1-1), (A-1)
(Compound 40)
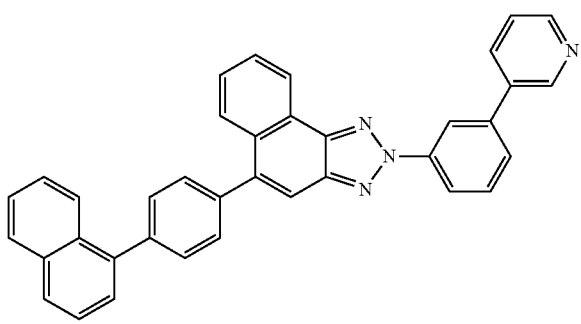
m = 1, X = C
Formulas (1-1), (A-1)
(Compound 41)
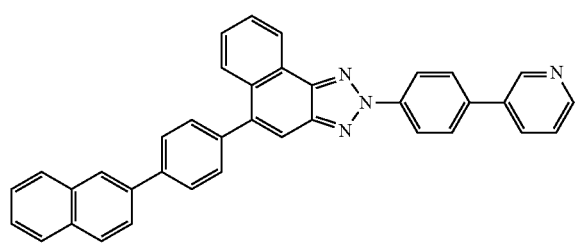
m = 1, X = C
Formulas (1-1), (A-1), (A-5)
(Compound 42)
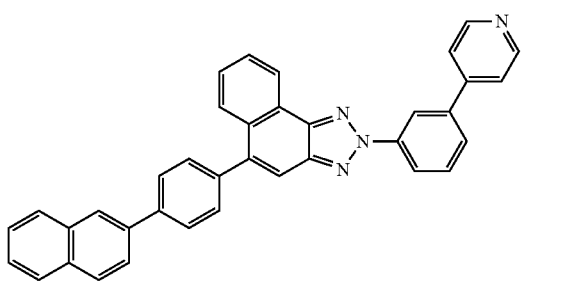
m = 1, X = C
Formulas (1-1), (A-1)

-continued
(Compound 43)
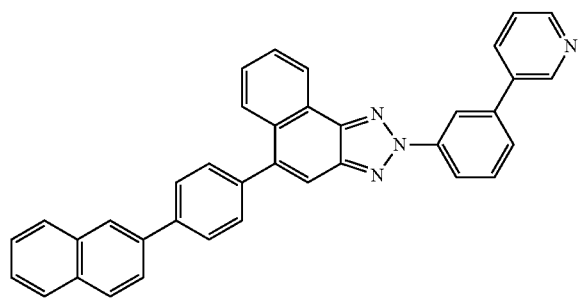
m = 1, X = C
Formulas (1-1), (A-1)
(Compound 44)
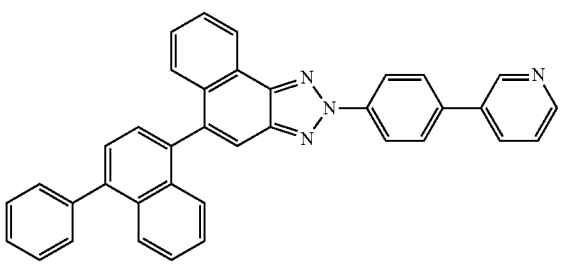
m = 1, X = C
Formulas (1-1), (A-1), (A-5)
(Compound 45)
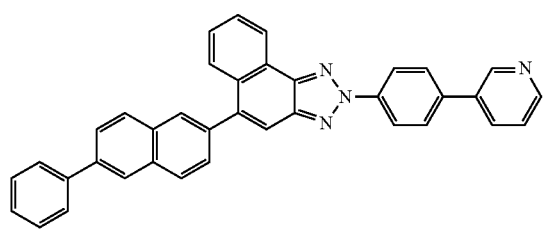
m = 1, X = C
Formulas (1-1), (A-1), (A-5)
(Compound 46)
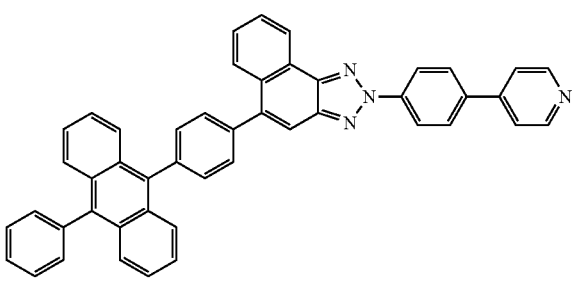
m = 1, X = C
Formulas (1-1), (A-1), (A-6)
(Compound 47)
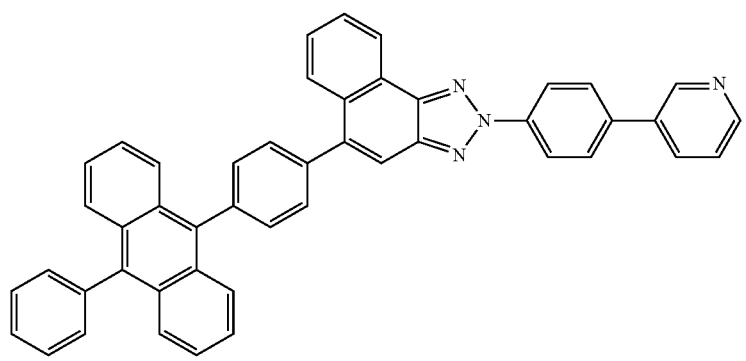
m = 1, X = C
Formulas (1-1), (A-1), (A-5)
(Compound 48)
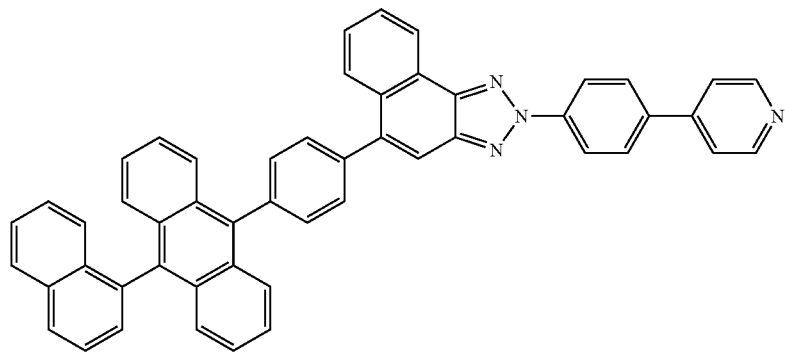
m = 1, X = C
Formulas (1-1), (A-1), (A-6)

-continued
(Compound 49)
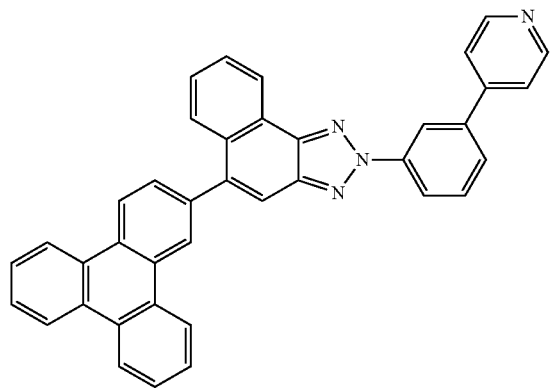
m = 1, X = C
Formulas (1-1), (A-1)
(Compound 50)
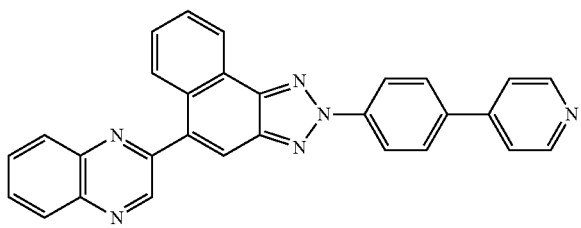
m = 1, X = C
Formulas (1-1), (A-1), (A-6)
(Compound 51)
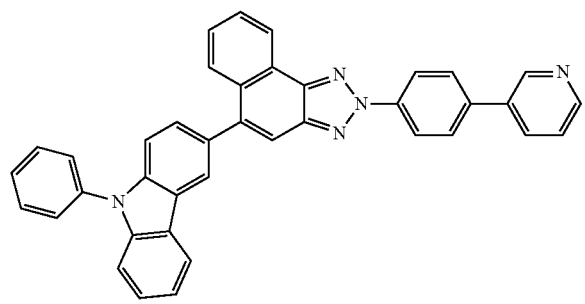
m = 1, X = C
Formulas (1-1), (A-1), (A-5)
(Compound 52)
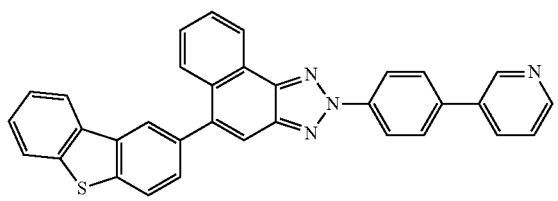
m = 1, X = C
Formulas (1-1), (A-1), (A-5)
(Compound 53)
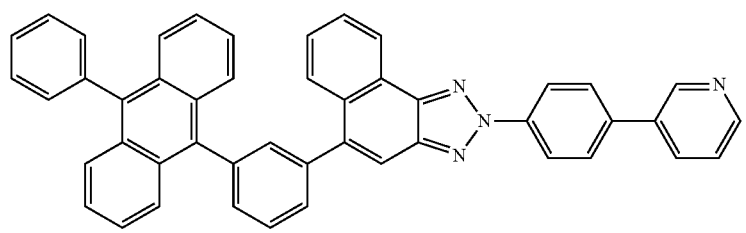
m = 1, X = C
Formulas (1-1), (A-1), (A-5)
(Compound 54)
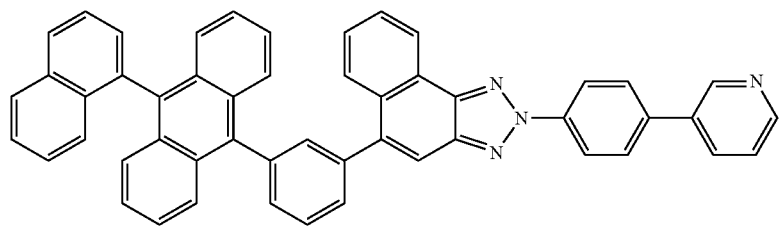
m = 1, X = C
Formulas (1-1), (A-1), (A-5)

-continued
(Compound 55)
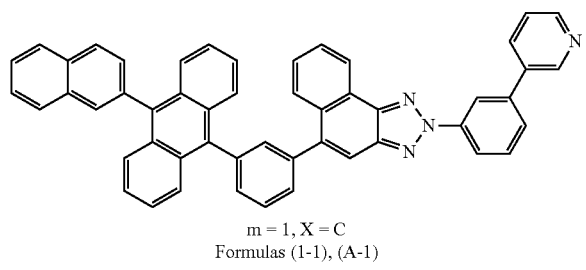
m = 1, X = C
Formulas (1-1), (A-1)
(Compound 56)
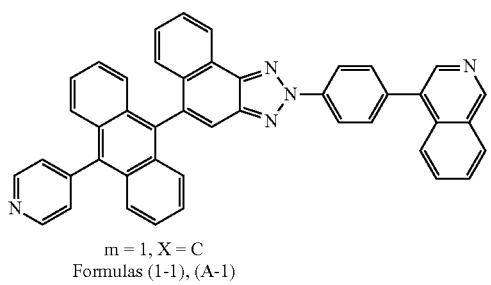
m = 1, X = C
Formulas (1-1), (A-1)
(Compound 57)
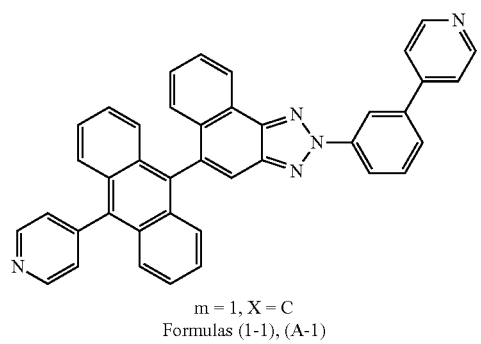
m = 1, X = C
Formulas (1-1), (A-1)
(Compound 58)
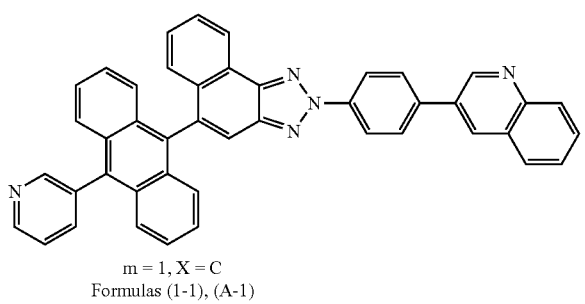
m = 1, X = C
Formulas (1-1), (A-1)
(Compound 59)
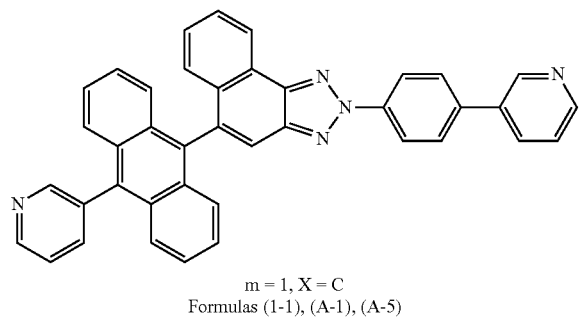
m = 1, X = C
Formulas (1-1), (A-1), (A-5)
(Compound 60)
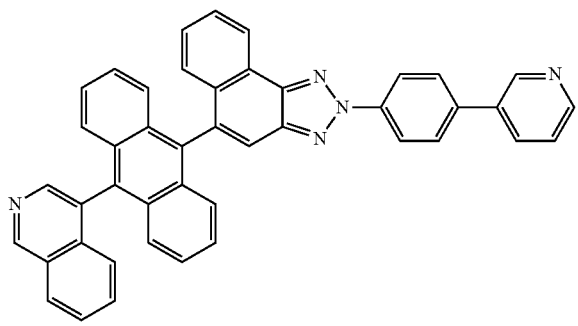
m = 1, X = C
Formulas (1-1), (A-1), (A-5)
(Compound 61)
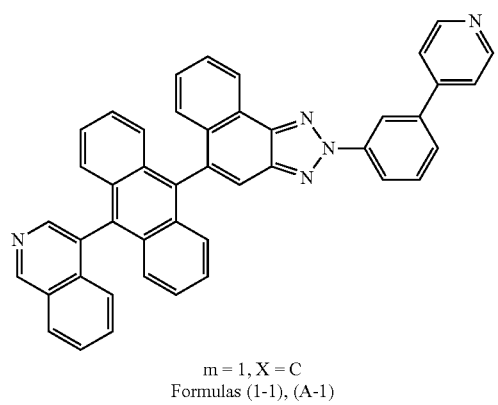
m = 1, X = C
Formulas (1-1), (A-1)
(Compound 62)
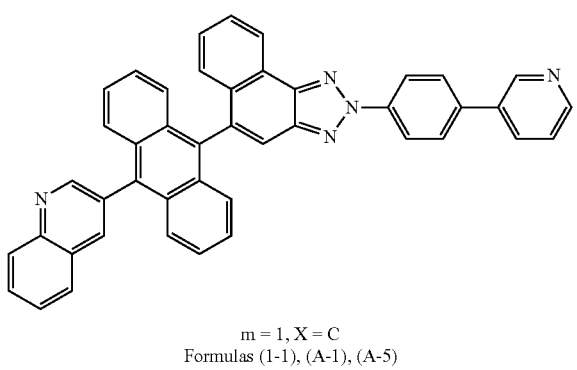
m = 1, X = C
Formulas (1-1), (A-1), (A-5)

-continued
(Compound 63)
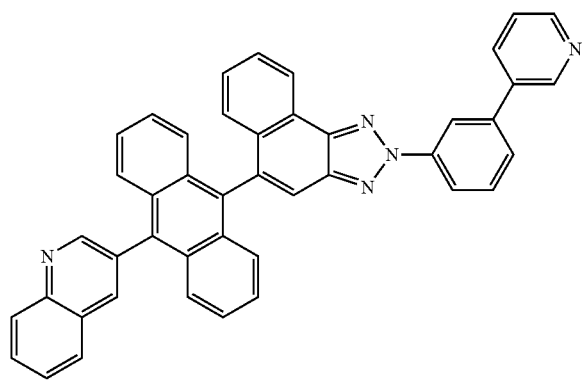
m = 1, X = C
Formulas (1-1), (A-1)
(Compound 64)
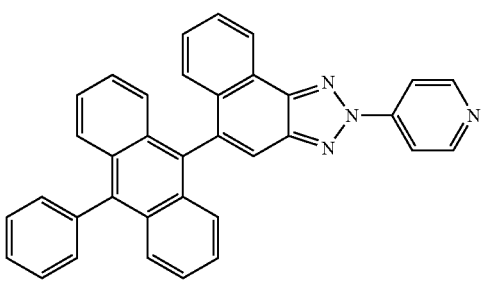
m = 0, X = C
Formula (1-1)
(Compound 65)
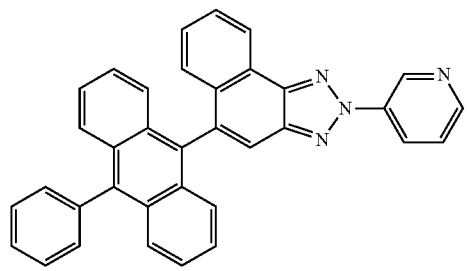
m = 1, X = C
Formula (1-1)
(Compound 66)
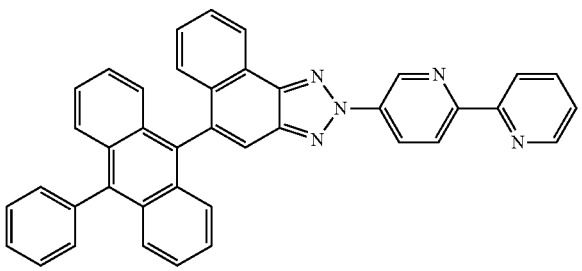
m = 1, X = N
Formula (1-1)
(Compound 67)
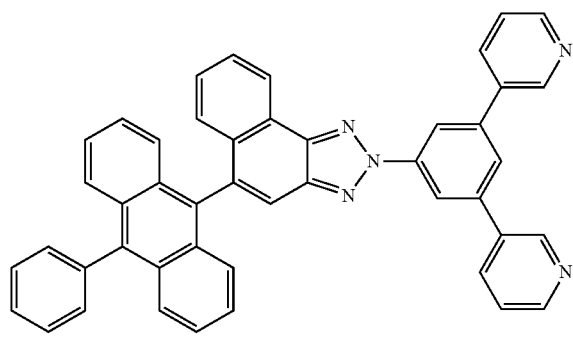
m = 1, X = C
Formulas (1-1), (A-1)
(Compound 68)
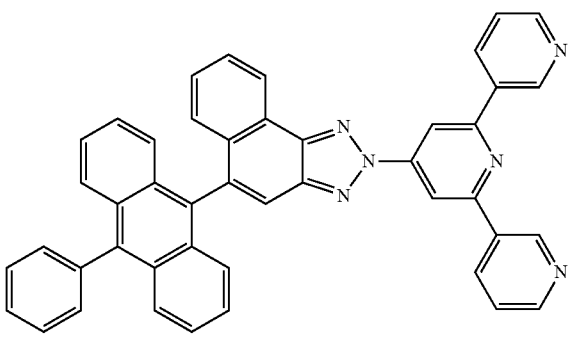
m = 1, X = N
Formulas (1-1)
(Compound 69)
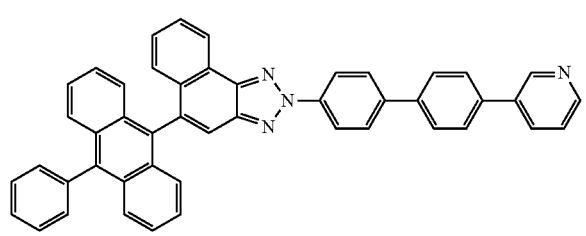
m = 2, X = C
Formulas (1-1), (A-3)
(Compound 70)
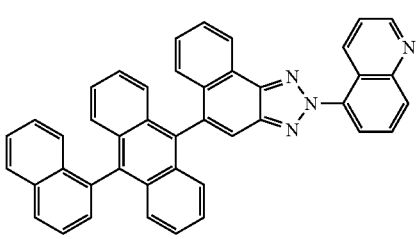
m = 0, X = C
Formula (1-1)

(Compound 71)
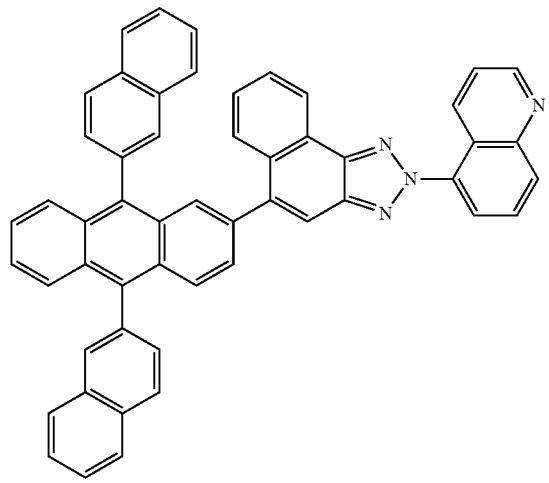
m = 0, X = C
Formula (1-1)
(Compound 72)
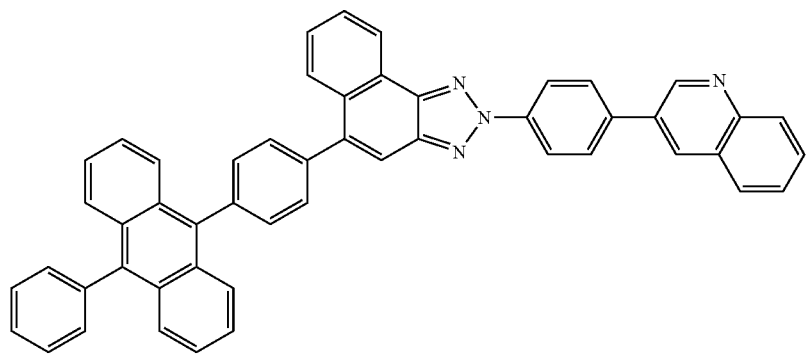
m = 1, X = C
Formulas (1-1), (A-1)
(Compound 73)
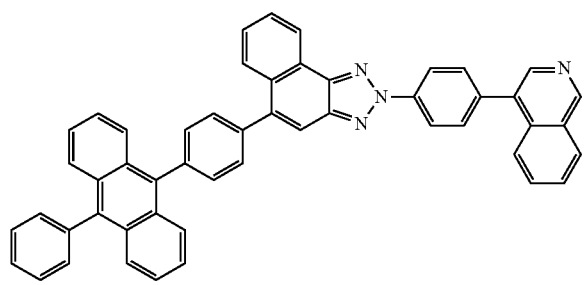
m = 1, X = C
Formulas (1-1), (A-1)
(Compound 74)
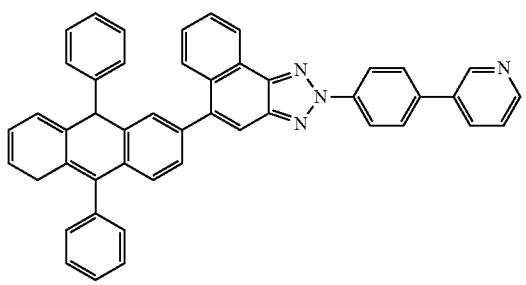
m = 1, X = C
Formulas (1-1), (A-1), (A-5)

-continued (Compound 75)

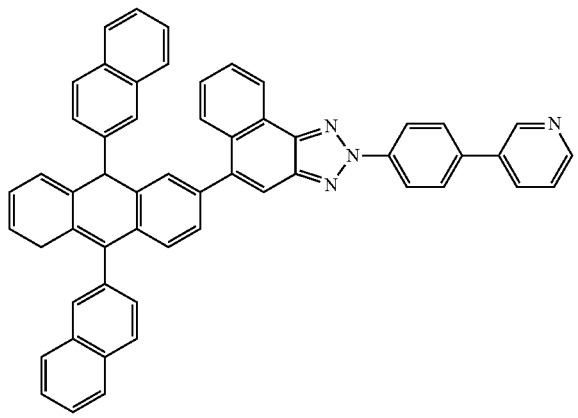

m = 1, X = C
Formulas (1-1), (A-1), (A-5)

(Compound 76)

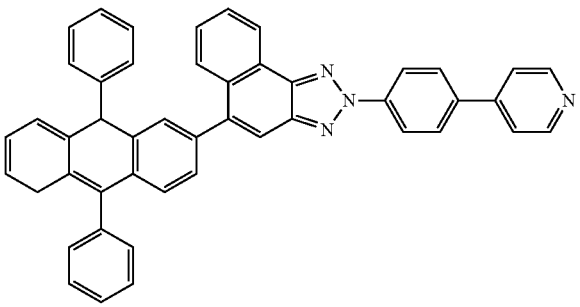

m = 1, X = C
Formulas (1-1), (A-1), (A-6)

(Compound 77)

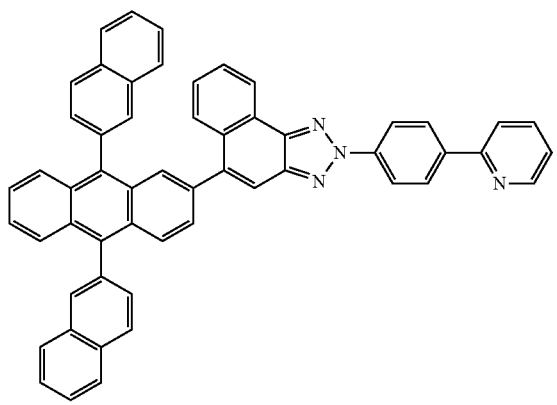

m = 1, X = C
Formulas (1-1), (A-1), (A-4)

(Compound 78)

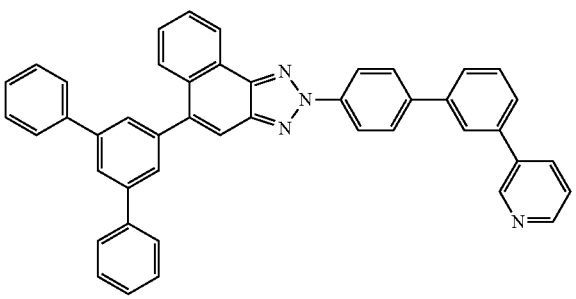

m = 2, X = C
Formulas (1-1), (A-3), (A-7)

(Compound 79)

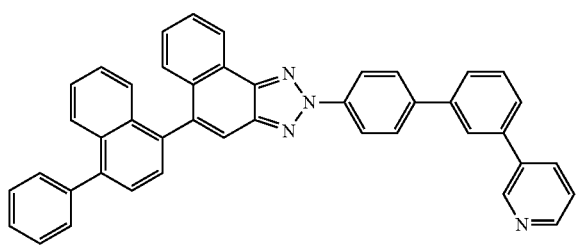

m = 2, X = C
Formulas (1-1), (A-3), (A-7)

The above naphthotriazole derivatives of the present invention have high glass transition points (Tg), make it possible to form a thin film having excellent heat resistance, stably maintain amorphous state and, therefore, stably maintain the state of a thin film. Besides, the naphthotriazole derivatives of the invention feature good electron injection rates, high electron moving rates and high hole-blocking power. For example, if the compound of the present invention is deposited to form a film of a thickness of 100 nm and if the film is measured for its work function, a very high value is exhibited.

Therefore, the naphthotriazole derivatives of the present invention are very useful as a material for forming an organic layer that is possessed by organic EL devices.

<Organic EL Devices>

Figure 9:
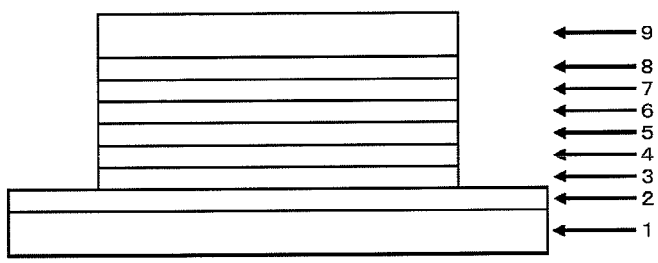
FIG. 9: View illustrating the structure of layers of an organic EL device.

The organic EL device having the organic layer formed by using the above naphthotriazole derivative of the present invention has a structure as shown, for example, in FIG. 9.

Namely, a transparent anode 2, a hole injection layer 3, a hole-transporting layer 4, a luminous layer 5, a hole-blocking layer 6, an electron-transporting layer 7, an electron injection layer 8 and a cathode 9 are formed on a glass substrate 1 (which may be any transparent substrate such as transparent resin substrate or the like substrate).

The organic EL device to which the naphthotriazole derivative of the present invention is applied is not limited to the one of the above layer structure, as a matter of course. For instance, the organic EL device may have an electron-blocking layer formed between the hole-transporting layer 4 and the luminous layer 5, or may have a simplified layer structure omitting the electron injection layer 8 and the hole injection layer 3. For instance, some layers can be omitted from the above multilayer structure. Namely, the organic EL device can be fabricated in a simple layer structure having the anode 2, hole-transporting layer 4, luminous layer 5, electron-transporting layer 7 and cathode 9 formed on the substrate 1.

That is, the naphthotriazole derivative of the invention is preferably used as a material for forming organic layers (e.g., luminous layer 5, hole-blocking layer 6, electron-transporting layer 7 and electron injection layer 8) between the anode 2 and the cathode 9.

In the organic EL device, the transparent anode 2 may be formed by using an electrode material which has been known per se, i.e., by vapor-depositing an electrode material having a large work function, such as ITO or gold on the substrate 1 (transparent substrate such as glass substrate or the like).

Further, the hole injection layer 3 can be formed on the transparent anode 2 by using the materials that have been known per se, such as those described below.

Porphyrin compound as represented by copper phthalocyanine;

Triphenylamine derivative of the star burst type;

Arylamine having a structure coupled via a single bond or a divalent group without hetero atom (e.g., trimer or tetramer of triphenylamine);

Acceptor-type heterocyclic compounds such as hexacyanoazatriphenylene; and

High molecular materials of the application type, such as poly(3,4-ethylenedioxythiophene) (PEDOT), poly(styrene sulfonate) (PSS), etc.

The layer (thin film) can be formed by using the above materials relying not only upon the vacuum evaporation method but also upon the known methods such as spin-coating method or ink-jet method. The layers described below, too, can similarly be formed by the vacuum evaporation, the spin-coating or the ink-jet method.

The hole-transporting layer 4, too, can be formed on the hole injection layer 3 by using a hole-transporting material that has been known per se. Representative examples of the hole-transporting materials are:
Benzidine derivatives such as,
  N,N'-Diphenyl-N,N'-di(m-tolyl)benzidine (hereinafter abbreviated as TPD);
  N,N'-Diphenyl-N,N'-di(α-naphthyl)benzidine (hereinafter abbreviated as NPD); and
  N,N,N',N'-Tetrabiphenylylbenzidine; and Amine derivatives such as,
  1,1-Bis[4-(di-4-tolylamino)phenyl]cyclohexane (hereinafter abbreviated as TAPC);
  Various triphenylamine trimers and tetramers; and
  The above-mentioned application-type high molecular materials that can also be used for forming the hole injection layer.

The compounds for forming the hole-transporting layer may be used alone to form a film or may be used being mixed together in two or more kinds to form a film. Or the above compounds may be used in one kind or in a plurality of kinds to form a plurality of layers, and a multiplicity of films formed by laminating such layers may be used as a hole-transporting layer.

It is, further, allowable to form a layer that serves as both the hole injection layer 3 and the hole-transporting layer 4. The hole injection transporting layer can be formed by being coated with a high molecular material such as PEDOT.

In forming the hole-transporting layer 4 (the same also holds for the hole injection layer 3, too), the material usually used for forming the layer may, further, be P-doped with a trisbromophenylaminehexachloroantimony or the like. It is also allowable to form the hole-transporting layer 4 (or the hole injection layer 3) by using a high molecular compound having a basic skeleton of TPD.

Further, as the electron-blocking layer (that can be formed between the hole-transporting layer 4 and the luminous layer 5) that has not been shown, there can be used a known electron-blocking compound having the electron-blocking action, such as carbazole derivative or a compound that has a triphenylsilyl group yet having a triarylamine structure. Described below are concrete examples of the carbazole derivative and the compound having the triarylamine structure.

<Carbazole Derivatives>
  4,4',4"-Tri(N-carbazolyl)triphenylamine (hereinafter abbreviated as TCTA);
  9,9-Bis[4-(carbazole-9-il)phenyl]fluorene;
  1,3-Bis(carbazole-9-il)benzene (hereinafter abbreviated as mCP); and
  2,2-Bis(4-carbazole-9-ilphenyl)adamantane (hereinafter abbreviated as Ad-Cz).

<Compounds Having a Triarylamine Structure>
  9-[4-(Carbazole-9-il)phenyl]-9-[4-(triphenylsilyl)phenyl]-9H-fluorene.

The electron-blocking layer is formed by using one, two or more kinds of the above known electron-blocking materials. It is, however, also allowable to form a plurality of layers by using one or a plurality of kinds of the electron-blocking materials, and use a multiplicity of films formed by laminating such layers as the electron-blocking layer.

The luminous layer 5 of the organic EL device can be formed by using the above naphthotriazole derivative of the invention as the luminous material. The luminous layer 5, however, can also be formed by using a metal complex of a quinolynol derivative as represented by $Alq_3$ as well as various metal complexes such as of zinc, beryllium and aluminum, and luminous materials such as anthracene derivative, bisstyrylbenzene derivative, pyrene derivative, oxazole derivative and polyparaphenylenevinylene derivative.

It is also allowable to constitute the luminous layer 5 by using a host material and a dopant material.

As the host material in this case, there can be used thiazole derivative, benzimidazole derivative and polydialkylfluorene derivative in addition to the above luminous materials.

As the dopant material, there can be used quinacridone, cumalin, rubrene, perylene and derivatives thereof, benzopyran derivative, Rhodamine derivative and aminostyryl derivative.

The luminous layer 5 too, can be formed in a single-layer structure by using one or two or more kinds of the luminous materials, or in a multi-layer structure by laminating a plurality of layers.

It is, further, allowable to form the luminous layer 5 by using a phosphorescent luminous material as the luminous material.

As the phosphorescent luminous material, there can be used a phosphorescent luminous body of a metal complex such as of iridium or platinum. For example, there can be used a green luminous phosphor such as Ir(ppy)$_3$, a blue luminous phosphor such as Flrpic or Flr$_6$, and a red luminous phosphor such as Btp$_2$Ir(acac). These phosphorescent luminous materials are used by being added to the hole injection transporting host material or to the electron-transporting host material.

As the hole injection transporting host material, there can be used 4,4'-di(N-carbazolyl)biphenyl (hereinafter abbreviated as CBP), or carbazole derivative such as TCTA or mCP.

As the electron-transporting host material, there can be used p-bis(triphenylsilyl)benzene (hereinafter abbreviated as UGH2) or 2,2',2"-(1,3,5-phenylene)-tris(1-phenyl-1H-benzimidazole) (hereinafter abbreviated as TPBI).

To avoid the concentration quenching, the host material is desirably doped with the phosphorescent luminous material in an amount in a range of 1 to 30% by weight relative to the whole luminous layer relying on the vacuum coevaporation.

As the luminous material, further, it is also allowable to use a material that emits retarded fluorescence, such as CDCB derivative like PIC-TRZ, CC2TA, PXZ-TRZ or 4CzIPN (see Appl. Phys. Let., 98, 083302 (2011)).

The hole-blocking layer 6 can also be formed between the luminous layer 5 and the electron-transporting layer 7 by using a known compound having the hole-blocking action in addition to using the naphthotriazole derivative of the present invention.

As the known compounds having the hole-blocking action, there can be exemplified the following compounds.

Phenanthrolene derivatives such as bathocuproin (hereinafter abbreviated as BCP) and the like;

Metal complexes of quinolinol derivatives such as aluminum (III) bis(2-methyl-8-quinolinato)-4-phenylphenolate (hereinafter abbreviated as BAlq) and the like;

Various rare earth complexes;

Triazole derivatives;

Triazine derivatives; and

Oxadiazole derivatives.

These materials can also be used for forming the electron-transporting layer 7 that will be described below. Moreover, the hole-blocking layer 6 and the electron-transporting layer 7 can be formed as one layer.

The hole-blocking layer 6, too, can be formed in the structure of a single layer or of a laminate of a multiplicity of layers, the layers being formed by using one kind, two kinds or more kinds of the above-mentioned compounds having hole-blocking action.

The electron-transporting layer 7 can be formed by using electron-transporting compounds that have been known per se. such as metal complexes of quinolinol derivatives like Alq$_3$, BAlq, as well as various metal complexes, triazole derivatives, triazine derivatives, oxadiazole derivatives, thiadiazole derivatives, carbodiimide derivatives, quinoxaline derivatives, phenanthroline derivatives and silole derivatives in addition to using the naphthotriazole derivatives of the present invention.

The electron-transporting layer 7, too, can be formed in the structure of a single layer or of a laminate of a multiplicity of layers, the layers being formed by using one kind, two kinds or more kinds of the above-mentioned electron-transporting compounds.

The electron injection layer 8, too, can be formed by using known compounds, i.e., by using alkali metal salts such as lithium fluoride and cesium fluoride, alkaline earth metal salts such as magnesium fluoride, and metal oxides such as aluminum oxide in addition to using the naphthotriazole derivatives of the present invention.

As the cathode 9 of the organic EL device, there can be used an electrode material having a low work function, such as aluminum, or an electrode material of an alloy having a lower work function, such as magnesium-silver alloy, magnesium-indium alloy or aluminum-magnesium alloy.

The organic EL device forming at least one of the organic layers (e.g., at least any one of electron injection layer 8, electron-transporting layer 7, hole-blocking layer 6 or luminous layer 5) by using the naphthotriazole derivative of the present invention, features a high luminous efficiency, a high power efficiency, a low practical driving voltage, a low luminance start voltage and very excellent durability.

The invention will now be more concretely described by way of Examples to which only, however, the invention is in no way limited.

Example 1

Synthesis of a 5-{10-(naphthalene-1-il)anthracene-9-il}-2-{4-(pyridine-3-il)phenyl}-2H-naphtho[1,2-d][1,2,3]triazole Synthesis of a Compound 9

(Compound 9)

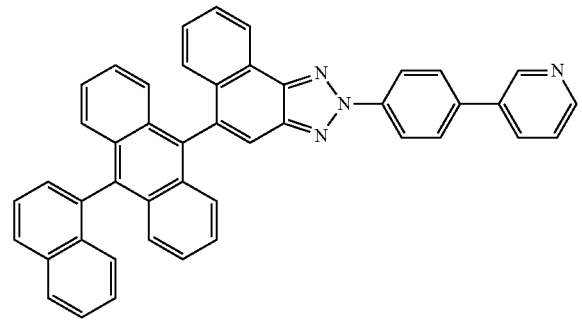

m = 1, X = C
Formulas (1-1), (A-1), (A-5)

| | |
|---|---:|
| 1-Bromo-4-nitrobenzene | 50 g, |
| 3-Pyridineboronic acid | 31.9 g, |
| 2M Potassium carbonate aqueous solution | 309 ml, |
| Toluene | 200 ml, |
| Ethanol | 40 ml, and |
| Tetrakistriphenylphosphine palladium(0) | 11.0 g, | were put into a reaction vessel purged with nitrogen, and were heated and refluxed for 14 hours with stirring. The reaction solution was concentrated, and the precipitated crystals were picked up by filtration. Through the dispersion washing with an isopropanol, there was obtained a grey powder of 3-(4-nitrophenyl)pyridine crystals in an amount of 43.5 g (yield, 88.8%).

| | |
|---|---|
| The thus obtained 3-(4-nitrophenyl)pyridine | 3.5 g, |
| 4-Bromo-1,2-diaminonaphthalene | 4.0 g, |
| Caustic soda and | 1.4 g, |
| Toluene | 50 ml, | were put into the reaction vessel purged with nitrogen, and were heated and refluxed for 7 hours with stirring.

100 Milliliters of toluene was added thereto to extract the reaction solution which was then concentrated under a reduced pressure and was refined by the column chromatography to obtain 2.14 g of a red powder of 4-bromo-2-{4-(pyridine-3-il)phenylazo}naphthyl-1-amine (first intermediate halide) crystals (yield, 30.3%).

| | |
|---|---|
| The thus obtained first intermediate halide | 2.0 g, |
| Iodobenzene diacetate | 2.6 g, and |
| Toluene | 20 ml, | were put into the reaction vessel purged with nitrogen, and were stirred at 92° C. for one hour.

The organic layer was picked up by the separating operation, concentrated under a reduced pressure and was refined by the column chromatography to obtain 1.2 g of a white powder of 5-bromo-2-{4-(pyridine-3-il)phenyl}-2H-naphtho[1,2-d][1,2,3]triazole (second intermediate halide) crystals (yield, 60.6%).

| | |
|---|---|
| The thus obtained second intermediate halide | 4.0 g, |
| (10-(Naphthalene-1-il)anthracene-9-il} boric acid | 3.8 g, |
| 2M Potassium carbonate aqueous solution | 15 ml, |
| Toluene | 40 ml, |
| Ethanol and | 16 ml, |
| Tetrakistriphenylphosphine palladium (0) | 0.1 g, | were put into the reaction vessel purged with nitrogen, and were heated and refluxed for 9 hours with stirring.

The organic layer was picked up by the separating operation, concentrated under a reduced pressure and was refined by the column chromatography to obtain 4.18 g of a faintly yellow powder of 5-{10-(naphthalene-1-il)anthracene-9-il)-2-{4-(pyridine-3-il)phenyl}-2H-naphtho[1,2-d][1,2,3]triazole (compound 9) (yield, 67.0%).

The obtained faintly yellow powder was identified for its structure by the NMR. FIG. 1 shows the results of the $^1$H-NMR measurement.

The following 28 signals of hydrogen were detected by the $^1$H-NMR (CDCl$_3$).

δ (ppm)=8.98 (1H)

8.87 (1H)

8.67 (1H)

8.61 (1H)

8.11 (2H)

8.05 (2H)

8.00 (1H)

7.84 (2H)

7.76-7.66 (6H)

7.53-7.21 (11H)

Example 2

Synthesis of a 5-(9,10-diphenylanthracene-2-il)-2-(4-(pyridine-3-il)phenyl)-2H-naphtho[1,2-d][1,2,3]triazole; (Synthesis of a Compound 74)

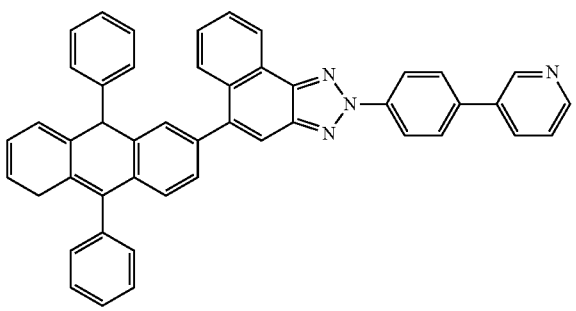

(Compound 74)

m = 1, X = C
Formulas (1-1), (A-1), (A-5)

| | |
|---|---|
| The second intermediate halide synthesized in Example 1 | 5.59 g, |
| {9,10-Diphenylanthracene-2-il} boronic acid | 6.25 g, |
| 2M Potassium carbonate aqueous solution | 14 ml, |
| 1,4-Dioxane and | 56 ml, |
| Tetrakistriphenylphosphine palladium (0) | 0.64 g, | were put into the reaction vessel purged with nitrogen, and were heated and refluxed for 4.0 hours with stirring.

The organic layer was picked up by the separating operation, concentrated under a reduced pressure and was refined by the column chromatography to obtain 6.36 g of a faintly yellowish white powder of 5-(9,10-diphenylanthracene-2-il)-2-{4-(pyridine-3-il)phenyl}-2H-naphtho[1,2-d][1,2,3]triazole (compound 74) (yield, 70.2%).

Figure 2:
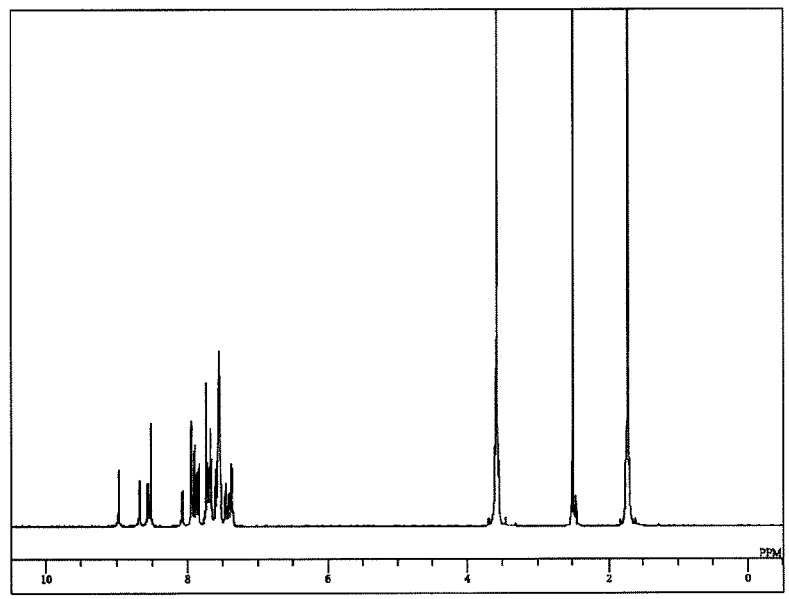
FIG. 2: ¹H-NMR chart of compound (compound 74) of Example 2.

The obtained faintly yellowish white powder was identified for its structure by the NMR. FIG. 2 shows the results of the $^1$H-NMR measurement.

The following 30 signals of hydrogen were detected by the $^1$H-NMR (THF-d8).

δ (ppm)=8.98 (1H)

8.69 (1H)

8.58 (1H)

8.53 (2H)

8.08 (1H)

7.94 (2H)

7.91 (1H)

7.88 (1H)

7.85 (1H)

7.74-7.66 (6H)

7.60-7.53 (9H)

7.46 (1H)

7.42 (1H)
7.37 (1H)

Example 3

Synthesis of a 5-(9,10-diphenylanthracene-2-il)-2-{4-(pyridine-4-il)phenyl}-2H-naphtho[1,2-d][1,2,3]triazole; (Synthesis of a Compound 76)

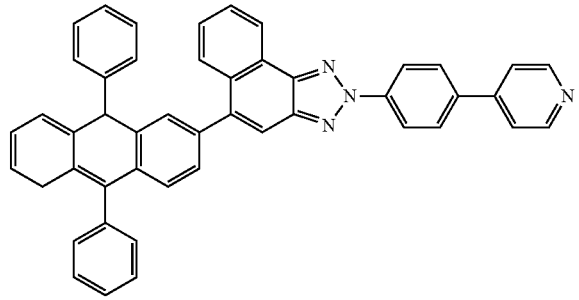

(Compound 76)

m = 1, X = C
Formulas (1-1), (A-1), (A-6)

| | |
|---|---|
| 1-Bromo-4-nitrobenzene | 50 g, |
| 4-Pyridineboronic acid | 31.9 g, |
| 2M Potassium carbonate aqueous solution | 309 ml, |
| Toluene | 200 ml, |
| Ethanol | 40 ml, and |
| Tetrakistriphenylphosphine palladium (0) | 11.0 g, | were put into a reaction vessel purged with nitrogen, and were heated and refluxed for 14 hours with stirring.

The reaction solution was concentrated, and the precipitated crystals were picked up by filtration. Through the dispersion washing with an isopropanol, there was obtained a grey powder of 4-(4-nitrophenyl)pyridine crystals in an amount of 41.8 g (yield, 85.4%).

| | |
|---|---|
| The thus obtained 4-(4-nitrophenyl)pyridine | 3.5 g, |
| 4-Bromo-1,2-diaminonaphthalene | 4.0 g, |
| Caustic soda | 1.4 g, and |
| Toluene | 50 ml, | were put into the reaction vessel purged with nitrogen, and were heated and refluxed for 7 hours with stirring.

100 Milliliters of toluene was added thereto to extract the reaction solution which was then concentrated under a reduced pressure and was refined by the column chromatography to obtain 2.2 g of a red powder of 4-bromo-2-{4-(pyridine-4-il)phenylazo}naphthyl-1-amine (first intermediate halide) crystals (yield, 31.5%).

| | |
|---|---|
| The thus obtained firstintermediate halide | 2.0 g, |
| Iodobenzene diacetate and | 2.6 g, |
| Toluene | 20 ml, | were put into the reaction vessel purged with nitrogen, and were stirred at 92° C. for one hour.

The organic layer was picked up by the separating operation, concentrated under a reduced pressure and was refined by the column chromatography to obtain 1.1 g of a white powder of 5-bromo-2-{4-(pyridine-4-il)phenyl}-2H-naphtho[1,2-d][1,2,3]triazole (second intermediate halide) crystals (yield, 57.8%).

| | |
|---|---|
| The thus obtained second intermediate halide | 5.59 g, |
| {9,10-Diphenylanthracene-2-il} boric acid | 6.25 g, |
| 2M Potassium carbonate aqueous solution | 14 ml, |
| 1,4-Dioxane and | 56 ml |
| Tetrakistriphenylphosphine palladium (0) | 0.64 g, | were put into the reaction vessel purged with nitrogen, and were heated and refluxed for 4.0 hours with stirring.

The organic layer was picked up by the separating operation, concentrated under a reduced pressure and was refined by the column chromatography to obtain 6.39 g of a faintly yellowish white powder of 5-(9,10-diphenylanthracene-2-il)-2-{4-(pyridine-4-il)phenyl}-2H-naphtho[1,2-d][1,2,3]triazole (compound 76) (yield, 70.5%).

Figure 3:
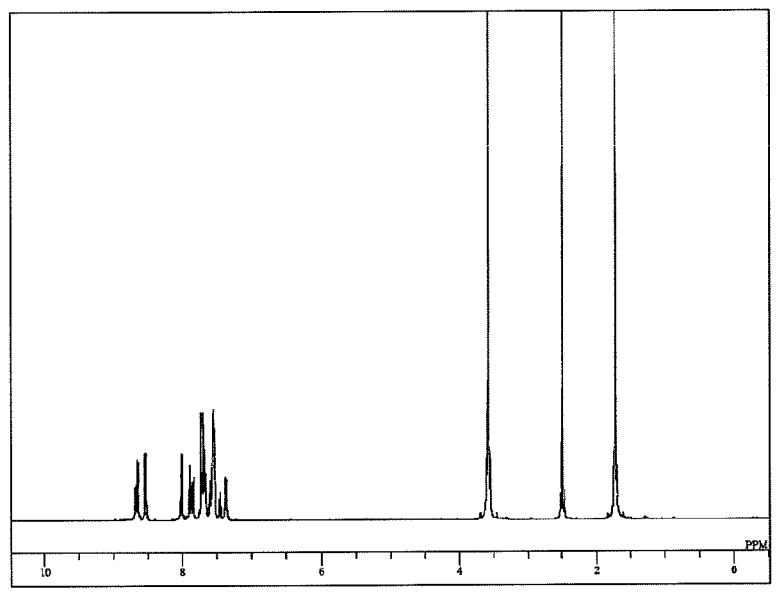
FIG. 3: ¹H-NMR chart of compound (compound 76) of Example 3.

The obtained faintly yellowish white powder was identified for its structure by the NMR. FIG. 3 shows the results of the $^1$H-NMR measurement.

The following 30 signals of hydrogen were detected by the $^1$H-NMR (THF-ds).
δ (ppm)=8.69 (1H)
8.65 (2H)
8.54 (2H)
8.02 (2H)
7.90 (1H)
7.88 (1H)
7.84 (1H)
7.74-7.61 (8H)
7.60-7.53 (9H)
7.46 (1H)
7.37 (2H)

Example 4

Synthesis of a 5-{9,10-bis(naphthalene-2-il)anthracene-2-il)-2-{4-(pyridine-3-il)phenyl}-2H-naphtho[1,2-d][1,2,3]triazole; (Synthesis of a Compound 75)

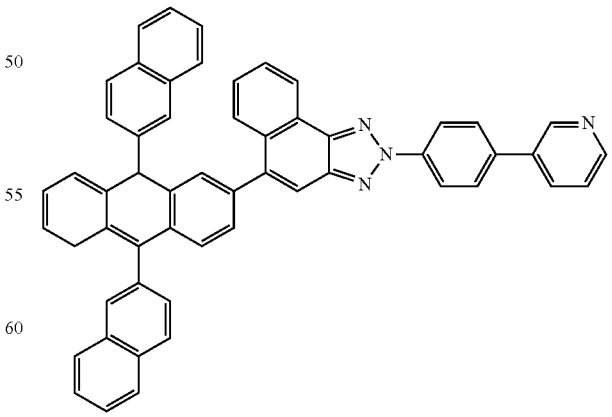

(Compound 75)

m = 1, X = C
Formulas (1-1), (A-1), (A-5)

Figure 4:
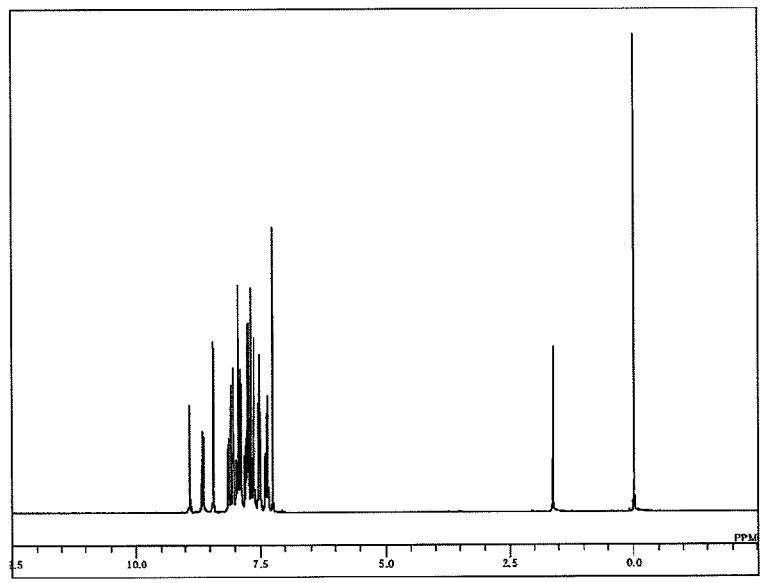
FIG. 4: ¹H-NMR chart of compound (compound 75) of Example 4.

| | |
|---|---|
| The second intermediate halide synthesized in Example 1 | 3.0 g, |
| {9,10-Bis(naphthalene-2-il)anthracene-2-il}boronic acid | 6.2 g, |
| 2M Potassium carbonate aqueous solution | 11 ml, |
| Toluene | 44 ml, |
| Ethanol and | 11 ml, |
| Tetrakistriphenylphosphine palladium (0) | 0.1 g, | were put into the reaction vessel purged with nitrogen, and were heated and refluxed for 22.0 hours with stirring. The organic layer was picked up by the separating operation, concentrated under a reduced pressure and was refined by the column chromatography to obtain 3.15 g of a faintly yellowish white powder of 5-{9,10-bis(naphthalene-2-il)anthracene-2-il}-2-{4-(pyridine-3-il)phenyl}-2H-naphtho[1,2-d][1,2,3]triazole (compound 75) (yield, 56.1%). The obtained faintly yellowish white powder was identified for its structure by the NMR. FIG. 4 shows the results of the $^1$H-NMR measurement. The following 34 signals of hydrogen were detected by the $^1$H-NMR (CDCl$_3$).

δ (ppm)=8.92 (1H)
8.67 (1H)
8.63 (1H)
8.45 (2H)
8.14 (1H)
8.10 (1H)
8.06 (3H)
7.93 (7H)
7.80-7.63 (10H)
7.54-7.50 (4H)
7.40 (1H)
7.36 (2H)

Example 5

Synthesis of a 5-{9,10-bis(naphthalene-2-il)anthracene-2-il}-2-{4-(pyridine-2-il)phenyl}-2H-naphtho[1,2-d][1,2,3]triazole; (Synthesis of a Compound 77)

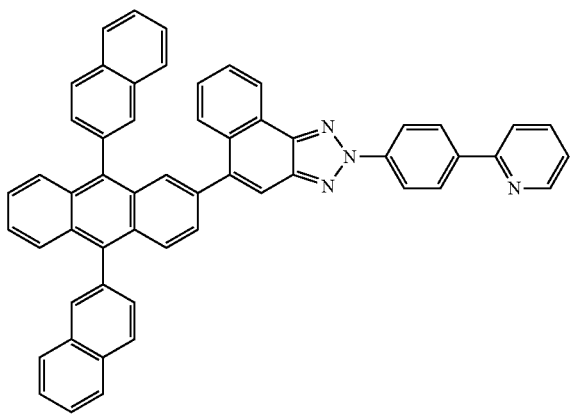

(Compound 77)

m = 1, X = C
Formulas (1-1), (A-1), (A-4)

| | |
|---|---|
| 1-Bromo-4-nitrobenzene | 50 g, |
| 3-Pyridineboronic acid | 31.9 g, |
| 2M Potassium carbonate aqueous solution | 309 ml, |
| Toluene | 200 ml, |
| Ethanol | 40 ml, and |
| Tetrakistriphenylphosphine palladium (0) | 11.0 g, | were put into a reaction vessel purged with nitrogen, and were heated and refluxed for 14 hours with stirring.

The reaction solution was concentrated, and the precipitated crystals were picked up by filtration. Through the dispersion washing with an isopropanol, there was obtained a grey powder of 2-(4-nitrophenyl)pyridine crystals in an amount of 41.5 g (yield, 84.8%).

| | |
|---|---|
| The thus obtained 2-(4-nitrophenyl)pyridine | 3.5 g, |
| 4-Bromo-1,2-diaminonaphthalene | 4.0 g, |
| Caustic soda and | 1.4 g, |
| Toluene | 50 ml, | were put into the reaction vessel purged with nitrogen, and were heated and refluxed for 7 hours with stirring.

100 Milliliters of toluene was added thereto to extract the reaction solution which was then concentrated under a reduced pressure and was refined by the column chromatography to obtain 2.33 g of a red powder of 4-bromo-2-{4-(pyridine-2-il)phenylazo}naphthyl-1-amine (first intermediate halide) crystals (yield, 32.9%).

| | |
|---|---|
| The thus obtained first intermediate halide | 2.0 g, |
| Iodobenzene diacetate | 2.6 g, and |
| Toluene | 20 ml, | were put into the reaction vessel purged with nitrogen, and were stirred at 92° C. for one hour.

The organic layer was picked up by the separating operation, concentrated under a reduced pressure and was refined by the column chromatography to obtain 1.28 g of a white powder of 5-bromo-2-{4-(pyridine-2-il)phenyl}-2H-naphtho[1,2-d][1,2,3]triazole (second intermediate halide) crystals (yield, 65.0%).

| | |
|---|---|
| The thus obtained second intermediate halide | 3.0 g, |
| {9,10-Bis(naphthalene-2-il)anthracene-2-il}boronic acid | 6.2 g, |
| 2M Potassium carbonate aqueous solution | 11 ml, |
| Toluene | 44 ml, |
| Ethanol and | 11 ml, |
| Tetrakistriphenylphosphine palladium (0) | 0.1 g, | were put into the reaction vessel purged with nitrogen, and were heated and refluxed for 14.0 hours with stirring.

The organic layer was picked up by the separating operation, concentrated under a reduced pressure and was refined by the column chromatography to obtain 3.04 g of a faintly yellowish green powder of 5-(9,10-bis(naphthalene-2-il)anthracene-2-il)-2-{4-(pyridine-2-il)phenyl}-2H-naphtho[1,2-d][1,2,3]triazole (compound 77) (yield, 54.3%).

Figure 5:
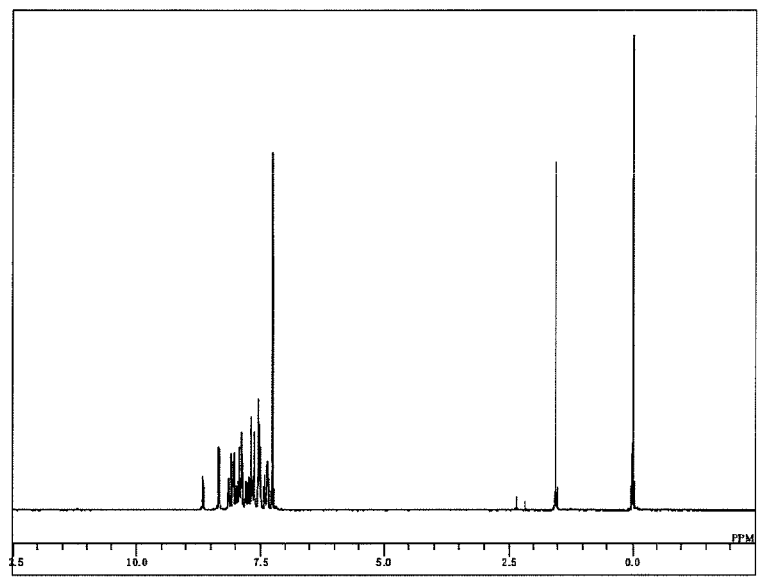
FIG. 5: ¹H-NMR chart of compound (compound 77) of Example 5.

The obtained faintly yellowish green powder was identified for its structure by the NMR. FIG. 5 shows the results of the $^1$H-NMR measurement.

The following 34 signals of hydrogen were detected by the 1H-NMR (CDCl₃).

δ (ppm)=8.66 (1H)
8.34 (2H)
8.14 (1H)
8.10 (1H)
8.05 (3H)
7.99 (3H)
7.86-7.95 (5H)
7.80 (1H)
7.77 (1N)
7.73 (5H)
7.65 (5H)
7.53 (6H)
7.42 (1H)
7.36 (2H)

Example 6

Synthesis of a 5-{3-(10-phenylanthracene-9-il)phenyl}-2-{4-(pyridine-3-il)phenyl}-2H-naphtho[1,2-d][1,2,3]triazole; (Synthesis of a Compound 53)

(Compound 53)

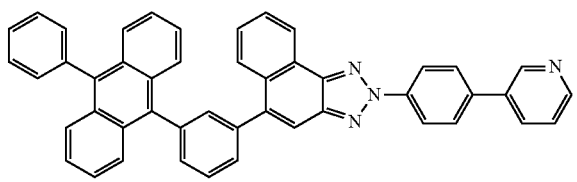

m = 1, X = C
Formulas (1-1), (A-1), (A-5)

| | |
|---|---|
| The second intermediate halide synthesized in Example 1 | 2.3 g, |
| 3-(10-Phenylanthracene-9-il) phenylboronic acid | 2.4 g, |
| 2M Potassium carbonate aqueous solution | 11 ml, |
| Toluene | 44 ml, |
| Ethanol and | 11 ml, |
| Tetrakistriphenylphosphine palladium (0) | 0.1 g, | were put into the reaction vessel purged with nitrogen, and were heated and refluxed for 22.0 hours with stirring.

The organic layer was picked up by the separating operation, concentrated under a reduced pressure and was refined by the column chromatography to obtain 1.80 g of a white powder of 5-{3-(10-phenylanthracene-9-il)phenyl}-2-(4-(pyridine-3-il)phenyl)-2H-naphtho[1,2-d][1,2,3]triazole (compound 53) (yield, 48.6%).

Figure 6:
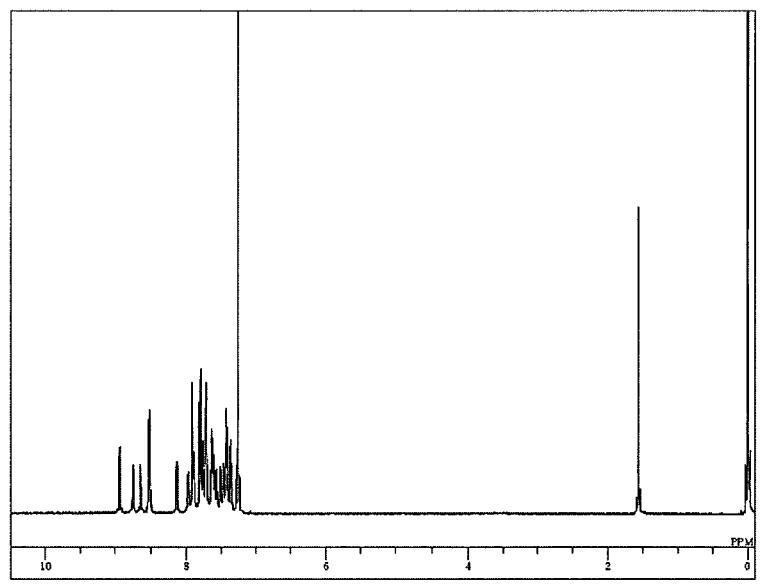
FIG. 6: ¹H-NMR chart of compound (compound 53) of Example 6.

The obtained white powder was identified for its structure by the NMR. FIG. 6 shows the results of the ¹H-NMR measurement.

The following 30 signals of hydrogen were detected by the ¹H-NMR (CDCl₃).

δ (ppm)=8.94 (1H)
8.75 (1H)
8.64 (1H)
8.51 (2H)
8.12 (1H)
7.92 (4H)
7.79-7.70 (8H)
7.60 (5H)
7.51-7.35 (7H)

Example 7

Synthesis of a 2-{3'-(pyridine-3-il)biphenyl-4-il}-5-{[1,1';3',1"]terphenyl-5'-il}-2H-naphtho[1,2-d][1,2,3]triazole Synthesis of a Compound 78

(Compound 78)

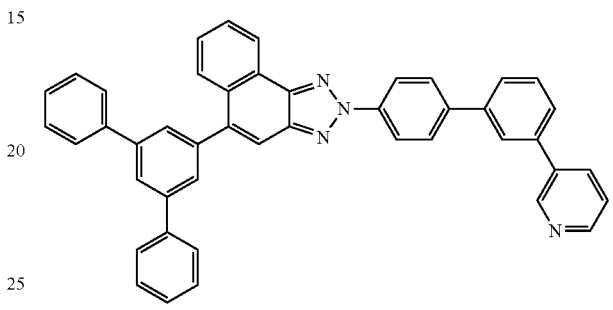

m = 2, X = C
Formulas (1-1), (A-3), (A-7)

| | |
|---|---|
| 1-Bromo-4-nitrobenzene | 50 g, |
| 3-(Pyridine-3-il)-phenylboronic acid | 31.9 g, |
| 2M Potassium carbonate aqueous solution | 309 ml, |
| Toluene | 200 ml, |
| Ethanol | 40 ml, and |
| Tetrakistriphenylphosphine palladium (0) | 11.0 g, | were put into a reaction vessel purged with nitrogen, and were heated and refluxed for 14 hours with stirring.

The reaction solution was concentrated, and the precipitated crystals were picked up by filtration. Through the dispersion washing with an isopropanol, there was obtained a grey powder of 3-(4'-nitrobiphenyl-3-il)pyridine crystals in an amount of 40.1 g (yield, 82.0%).

| | |
|---|---|
| The thus obtained 3-(4'-nitrobiphenyl-3-il)pyridine | 3.5 g, |
| 4-Bromo-1,2-diaminonaphthalene | 4.0 g, |
| Caustic soda and | 1.4 g, |
| Toluene | 50 ml, | were put into the reaction vessel purged with nitrogen, and were heated and refluxed for 9 hours with stirring.

100 Milliliters of toluene was added thereto to extract the reaction solution which was then concentrated under a reduced pressure and was refined by the column chromatography to obtain 2.50 g of a red powder of 4-bromo-2-[{3'-(pyridine-3-il)biphenyl-4-il}azo]naphthyl-1-amine (first intermediate halide) crystals (yield, 35.2%).

| | |
|---|---|
| The thus obtained first intermediate halide | 2.0 g, |
| Iodobenzene diacetate | 2.6 g, and |
| Toluene | 20 ml, | were put into the reaction vessel purged with nitrogen, and were stirred at 92° C. for one hour.

The organic layer was picked up by the separating operation, concentrated under a reduced pressure and was refined by the column chromatography to obtain 1.28 g of a white powder of 5-bromo-2-{3'-(pyridine-3-il)biphenyl-4-il}-2H-naphtho[1,2-d][1,2,3]triazole (second intermediate halide) crystals (yield, 65.0%).

| | |
|---|---|
| The thus obtained second intermediate halide | 3.0 g, |
| 3,5-Diphenyl-phenylboronic acid | 1.9 g, |
| 2M Potassium carbonate aqueous solution | 11 ml, |
| Toluene | 44 ml, |
| Ethanol and | 11 ml, |
| Tetrakistriphenylphosphine palladium (0) | 0.1 g, | were put into the reaction vessel purged with nitrogen, and were heated and refluxed for 12.0 hours with stirring.

The organic layer was picked up by the separating operation, concentrated under a reduced pressure and was refined by the column chromatography to obtain 1.68 g of a faintly yellowish green powder of 2-{3'-(pyridine-3-il)biphenyl-4-il}-5-{[1,1';3',1'']terphenyl-5'-il}-2H-naphtho[1,2-d][1,2,3]triazole (compound 78) (yield, 30.4%).

Figure 7:
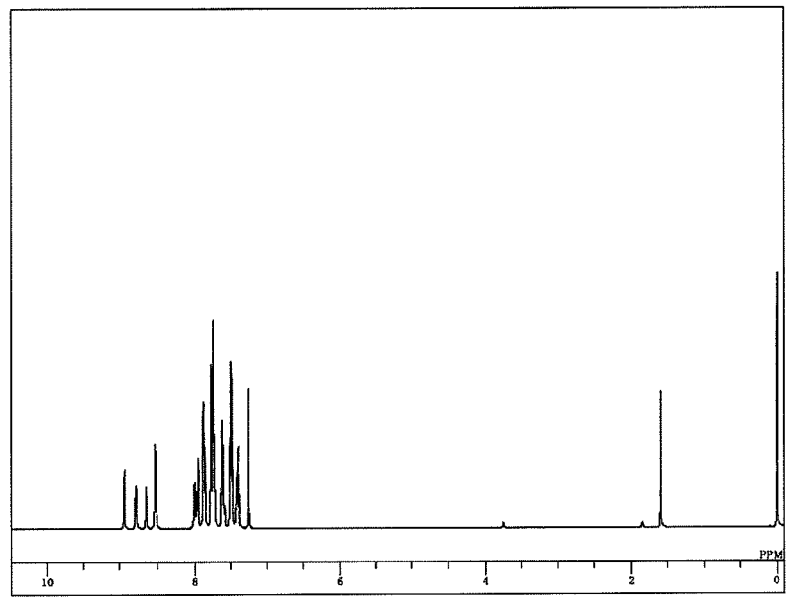
FIG. 7: ¹H-NMR chart of compound (compound 78) of Example 7.

The obtained faintly yellowish green powder was identified for its structure by the NMR. FIG. 7 shows the results of the $^1$H-NMR measurement.

The following 30 signals of hydrogen were detected by the $^1$H-NMR (CDCl$_3$).

δ (ppm)=8.95 (1H)
8.78 (1H)
8.65 (1H)
8.52 (2H)
7.94-8.01 (3H)
7.87 (4H)
7.71-7.77 (8H)
7.60 (3H)
7.49 (4H)
7.41 (3H)

Example 8

Synthesis of a 5-(4-phenylnaphthalene-1-il)-2-{3'-(pyridine-3-il)biphenyl-4-il}-2H-naphtho[1,2-d][1,2,3]triazole Synthesis of a Compound 79

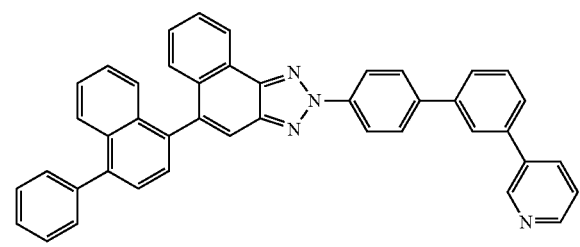

(Compound 79)

m = 2, X = C
Formulas (1-1), (A-3), (A-7)

| | |
|---|---|
| The second intermediate halide synthesized in Example 7 | 3.0 g, |
| 3,5-Diphenyl-phenylboronic acid | 4.0 g, |
| 4,4,5,5-Tetramethyl-2-(4-phenylnaphthalene-1-il)-[1,3,2] dioxaboronic acid ester | 3.0 g, |
| 2M Potassium carbonate aqueous solution | 11 ml, |
| Toluene | 44 ml, |
| Ethanol and | 11 ml, |
| Tetrakistriphenylphosphine palladium (0) | 0.1 g, | were put into the reaction vessel purged with nitrogen, and were heated and refluxed for 12.0 hours with stirring.

The organic layer was picked up by the separating operation, concentrated under a reduced pressure and was refined by the column chromatography to obtain 3.49 g of a faintly yellowish green powder of 5-(4-phenylnaphthalene-1-il)-2-{3'-(pyridine-3-il)biphenyl-4-il}-2H-naphtho[1,2-d][1,2,3]triazole (compound 79) (yield, 69.4%).

Figure 8:
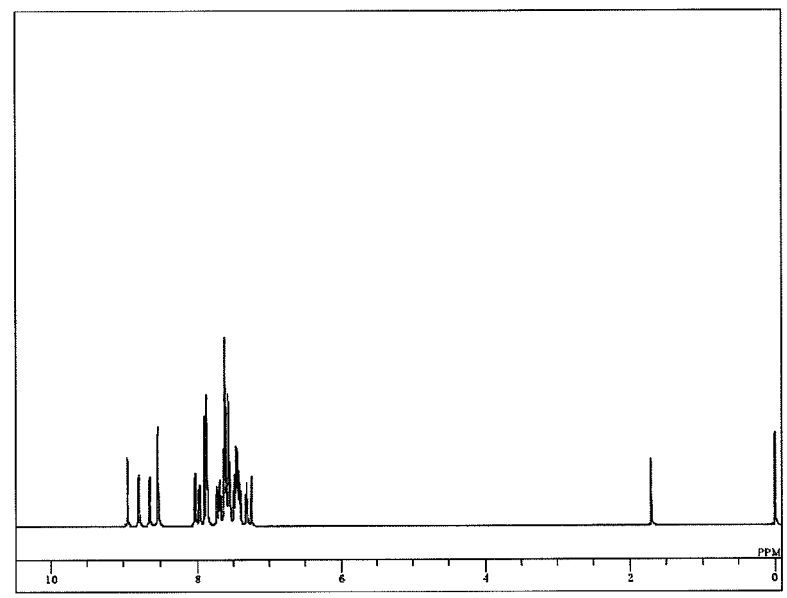
FIG. 8: $^1$H-NMR chart of compound (compound 79) of Example 8.

The obtained faintly yellowish green powder was identified for its structure by the NMR. FIG. 8 shows the results of the $^1$H-NMR measurement.

The following 28 signals of hydrogen were detected by the $^1$H-NMR (CDCl$_3$).

δ (ppm)=8.95 (1H)
8.79 (1H)
8.65 (1H)
8.54 (2H)
8.03 (1H)
7.96 (1H)
7.88 (4H)
7.72 (1H)
7.68 (1H)
7.62 (5H)
7.54-7.57 (5H)
7.45 (6H)

Example 9

By using a highly sensitive differential scanning calorimeter (DSC3100S manufactured by Bruker AXS Co.), the compounds of the present invention obtained in the above Examples were measured for their melting points and glass transition points. The results were as follows:

| Compound Nos. | Melting points | Glass transition points |
|---|---|---|
| Compound 9 | 362° C. | 185° C. |
| Compound 74 | 273° C. | 172° C. |
| Compound 76 | 394° C. | 171° C. |
| Compound 75 | 315° C. | 192° C. |
| Compound 77 | 358° C. | 175° C. |
| Compound 53 | 322° C. | 148° C. |
| Compound 78 | 273° C. | 108° C. |
| Compound 79 | 228° C. | 112° C. |

As will be understood from the above results, the compounds of the present invention have glass transition points which are not lower than 100° C. indicating that the thin films formed by using the compounds of the invention maintain stability (remain stable).

Example 10

By using the compounds of the invention obtained in the above Examples, films were vapor-deposited in a thickness of 100 nm on an ITO substrate and were measured for their work functions by using an apparatus for measuring ionization potentials (Model PYS-202 manufactured by Sumitomo Jukikai Kogyo Co.). The results were as follows:

| Compound Nos. | Work functions |
| --- | --- |
| Compound 9 | 6.13 eV |
| Compound 74 | 6.02 eV |
| Compound 76 | 6.05 eV |
| Compound 75 | 5.96 eV |
| Compound 77 | 5.84 eV |
| Compound 53 | 6.05 eV |

As described above, the compounds of the present invention have values larger than a work function of 5.4 eV possessed by general hole-transporting materials such as NPD, TPD and the like, and have large hole-blocking powers.

Example 11

An organic EL device of a layer structure shown in FIG. 9 was fabricated by vapor-depositing a hole injection layer 3, a hole-transporting layer 4, a luminous layer 5, a hole-blocking layer 6, an electron-transporting layer 7, an electron injection layer 8 and a cathode (aluminum electrode) 9 in this order on a glass substrate 1 on which an ITO electrode has been formed in advance as a transparent anode 2.

Concretely, the glass substrate 1 on which the ITO film has been formed in a thickness of 150 nm was washed with an organic solvent and was, thereafter, washed on its surfaces by an oxygen plasma treatment. Thereafter, the glass substrate with the ITO electrode was placed in a vacuum evaporation machine, and the pressure therein was reduced down to 0.001 Pa or lower.

<

Next, as the hole injection layer 3, a compound 80 of the following structural formula was vapor-deposited at a deposition rate of 6 nm/min. in a thickness of 20 nm so as to cover the transparent anode 2.

(Compound 80)

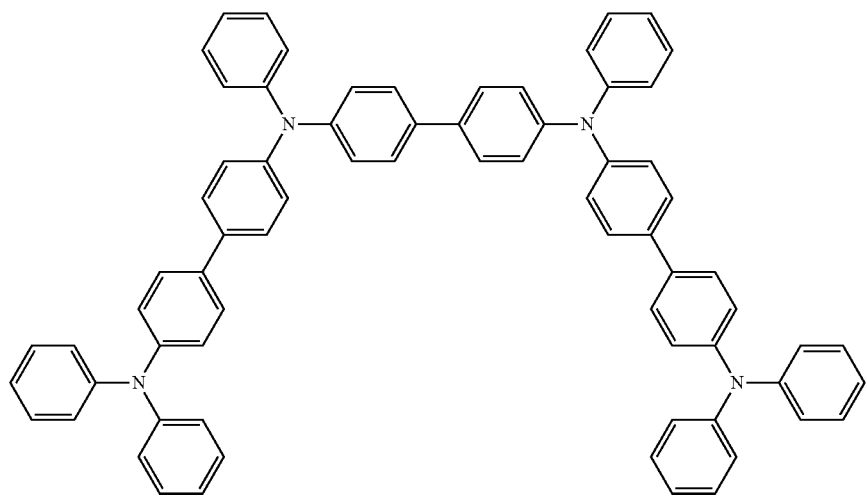

On the hole injection layer 3, a compound 81 of the following structural formula was vapor-deposited as the hole-transporting layer 4 at a deposition rate of 6 nm/min. in a thickness of 40 nm.

(Compound 81)

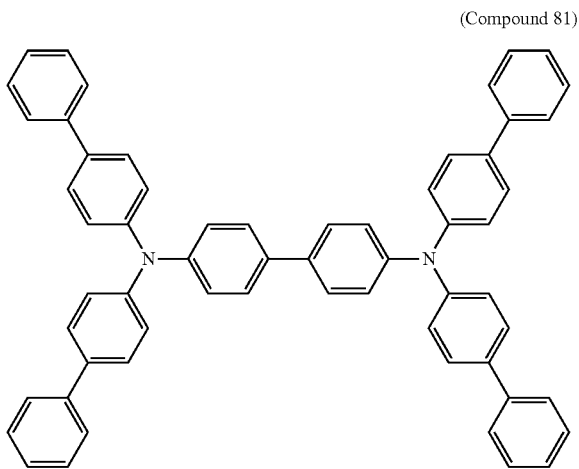 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]

On the hole-transporting layer 4, the luminous layer 5 was formed in a thickness of 30 nm by two-way-depositing a compound 82 of the following structural formula and a compound 83 of the following structural formula at a deposition rate of compound 82/compound 83 was 5/95.

(Compound 82)

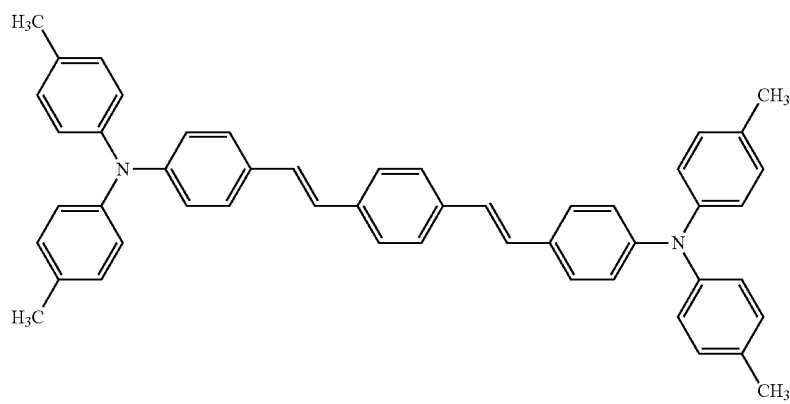

(Compound 83)

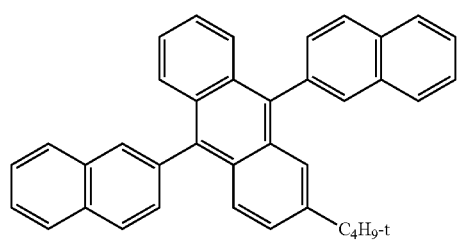

On the luminous layer 5, the compound 9 of the invention synthesized in Example 1 was vapor-deposited at a deposition rate of 6 nm/min. in a thickness of 30 nm so as to work both as the hole-blocking layer 6 and the electron-transporting layer 7.

On the thus formed hole-blocking layer/electron-transporting layer 6 and 7, the electron injection layer 8 was formed in a thickness of 0.5 nm by vapor-depositing lithium fluoride at a deposition rate of 0.6 nm/min.

Finally, aluminum was vapor-deposited in a thickness of 150 nm to form the cathode 9. The thus fabricated organic EL device was measured for its properties in the atmosphere at normal temperature.

The organic EL device forming an organic layer (hole-blocking layer/electron-transporting layer) by using the compound 9 of the invention was impressed with a DC voltage to measure the luminous properties which were as shown in Table 1.

Example 12

An organic EL device was fabricated under the same conditions as in Example 11 but using the compound 53 of Example 6 as the material for forming the hole-blocking layer/electron-transporting layer 6 and 7 instead of using the compound 9 of the invention synthesized in Example 1. The organic EL device was measured for its properties in the atmosphere at normal temperature. The organic EL device was impressed with a DC voltage to measure the luminous properties which were as shown in Table 1.

Example 13

An organic EL device was fabricated under the same conditions as in Example 11 but using the compound 74 of Example 2 as the material for forming the hole-blocking layer/electron-transporting layer 6 and 7 instead of using the compound 9 of Example 1. The thus fabricated organic EL device was measured for its properties in the atmosphere at normal temperature. The thus fabricated organic EL device was impressed with a DC voltage to measure the luminous properties which were as shown in Table 1.

Example 14

An organic EL device was fabricated under the same conditions as in Example 11 but using the compound 75 of Example 4 as the material for forming the hole-blocking layer/electron-transporting layer 6 and 7 instead of using the compound 9 of Example 1. The thus fabricated organic EL device was measured for its properties in the atmosphere at normal temperature. The thus fabricated organic EL device was impressed with a DC voltage to measure the luminous properties which were as shown in Table 1.

Example 15

An organic EL device was fabricated under the same conditions as in Example 11 but using the compound 76 of Example 3 as the material for forming the hole-blocking layer/electron-transporting layer 6 and 7 instead of using the compound 9 of Example 1. The thus fabricated organic EL device was measured for its properties in the atmosphere at normal temperature. The thus fabricated organic EL device was impressed with a DC voltage to measure the luminous properties which were as shown in Table 1.

Example 16

An organic EL device was fabricated under the same conditions as in Example 11 but using the compound 77 of Example 5 as the material for forming the hole-blocking layer/electron-transporting layer 6 and 7 instead of using the compound 9 of Example 1. The thus fabricated organic EL device was measured for its properties in the atmosphere at normal temperature. The thus fabricated organic EL device was impressed with a DC voltage to measure the luminous properties which were as shown in Table 1.

Comparative Example 1

For comparison, an organic EL device was fabricated under the same conditions as in Example 11 but using the compound 84 of the following structural formula disclosed in WO2003/060956 as the material for forming the hole-blocking layer/electron-transporting layer 6 and 7 instead of using the compound 9 of Example 1.

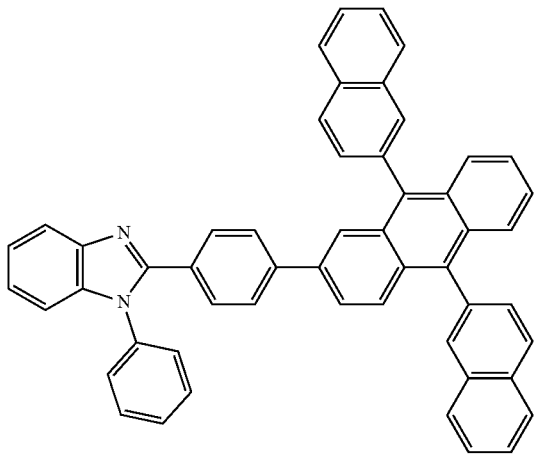

(Compound 84)

The thus fabricated organic EL device was measured for its properties in the atmosphere at normal temperature. The thus fabricated organic EL device was impressed with a DC voltage to measure the luminous properties which were as shown in Table 1.

TABLE 1

|  |  | Voltage [V] (@10 mA/cm$^2$) | Brightness [cd/m$^2$] (@10 mA/cm$^2$) | Current efficiency [cd/A] (@10 mA/cm$^2$) | Power efficiency [lm/W] (@ 10 mA/cm$^2$) |
|---|---|---|---|---|---|
| Example 11 | compound 9 | 5.65 | 840 | 8.40 | 4.67 |
| Example 12 | compound 53 | 5.83 | 887 | 8.87 | 4.78 |
| Example 13 | compound 74 | 5.26 | 974 | 9.74 | 5.81 |
| Example 14 | compound 75 | 5.19 | 983 | 9.83 | 5.95 |
| Example 15 | compound 76 | 5.29 | 971 | 9.71 | 5.76 |
| Example 16 | compound 77 | 5.68 | 965 | 9.65 | 5.33 |
| Comp. Ex. 1 | compound 84 | 5.95 | 7.92 | 7.92 | 4.19 |

As for the driving voltage at a current density of 10 mA/cm$^2$ as shown in Table 1, Examples 11 to 16 of the invention have driving voltages of as low as 5.19 to 5.83 V as compared to 5.95 V of the organic EL device (Comparative Example 1) that uses the compound 84 of the above structural formula.

When a current is flown at a density of 10 mA/cm$^2$, further, Examples 11 to 16 of the invention exhibit brightnesses of from 840 to 983 cd/m$^2$ which are great improvements over 792 cd/m$^2$ of Comparative Example 1.

Further, at a current density of 10 mA/cm$^2$, Examples 11 to 16 of the invention exhibit luminous efficiencies (current efficiencies) of from 8.40 to 9.87 cd/A which are great improvements over 7.92 cd/A of Comparative Example 1.

At the current density of 10 mA/cm$^2$, further, Examples 11 to 16 of the invention exhibit power efficiencies of from 4.67 to 5.95 lm/W which are great improvements over 4.19 lm/W of Comparative Example 1.

It will, therefore, be learned that the organic EL device of the present invention features excellent luminous efficiency and power efficiency as compared to the device that uses the compound 84 of the above general formula that is a widely employed electron-transporting material, and is capable of achieving a conspicuous decrease in the practical driving voltage.

From a conspicuous decrease in the driving voltage attained by the organic EL device using the naphthotriazole derivative of the present invention that has a naphthotriazole ring structure, it is presumed that the rate of electron migration in the naphthotriazole derivative is very larger than that of the compound 84 of the above structural formula that is a widely used electron-transporting material.

INDUSTRIAL APPLICABILITY

The naphthotriazole derivative of the present invention has good electron injection property and excellent hole-blocking power, remains stable in its thin film state, and can be used as an excellent compound for fabricating the organic EL devices. Upon fabricating the organic EL devices by using the above compound, further, it is allowed to attain a high luminous efficiency and power efficiency while lowering the practical driving voltage and improving the durability. Its use can, therefore, be expanded to, for example, domestic appliances and illumination equipment.

DESCRIPTION OF SYMBOLS 1 glass substrate
2 transparent anode
3 hole injection layer
4 hole-transporting layer
5 luminous layer
6 hole-blocking layer
7 electron-transporting layer
8 electron injection layer
9 cathode

The invention claimed is:
1. Naphthotriazole derivatives represented by the following general formula (1),

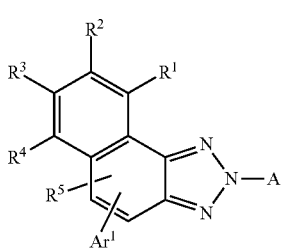

wherein,
Ar$^1$ is an aromatic hydrocarbon group,
R$^1$ to R$^5$ may be the same or different, and are hydrogen atoms, deuterium atoms, fluorine atoms, chlorine atoms, cyano groups, alkyl groups having 1 to 6 carbon atoms or aromatic hydrocarbon groups,
A is a monovalent group represented by the following structural formula (1a),

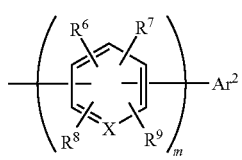

wherein,
m is an integer of 0, 1 or 2,
Ar$^2$ is a nitrogen-containing aromatic heterocyclic group,
R$^6$ to R$^9$ may be the same or different, and are hydrogen atoms, deuterium atoms, fluorine atoms, chlorine atoms, cyano groups, alkyl groups having 1 to 6 carbon atoms, aromatic hydrocarbon groups or aromatic heterocyclic groups,
X is a carbon atom or a nitrogen atom,
wherein if X is a nitrogen atom, R$^9$ is not present on the ring that includes the nitrogen atoms, if m is 0, Ar$^2$ is directly bonded to the nitrogen atom in the triazole ring and if m is 2, the plurality of R$^6$ to R$^9$ and X may be the same or different from each other,
wherein the aromatic hydrocarbon group represented by Ar$^1$ may not have a substituent or may have a substituent other than an aromatic heterocyclic group, and
wherein the aromatic hydrocarbon groups represented by R$^1$ to R$^5$ may not have a substituent or may have a substituent other than an aromatic heterocyclic group.

2. Naphthotriazole derivatives according to claim 1, wherein the group Ar$^1$ in said general formula (1) is bonded to the fourth position of a naphthalene ring in a naphthotriazole ring.

3. Naphthotriazole derivatives according to claim 1, wherein in said general formula (1), m is 0 in the structural formula (1a).

4. Naphthotriazole derivatives according to claim 1, wherein in said general formula (1), m is 1 in the structural formula (1a).

5. Naphthotriazole derivatives according to claim 1, wherein in said general formula (1), m is 2 in the structural formula (1a).

6. Naphthotriazole derivatives according to claim 1, wherein in said general formula (1), A is a monovalent group represented by any one of the following structural formula (A-1), (A-2) or (A-3),

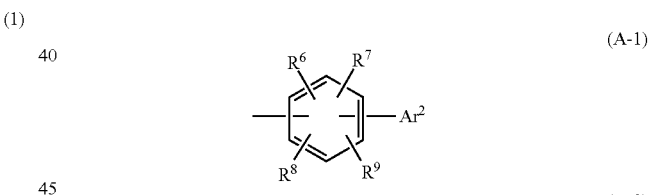

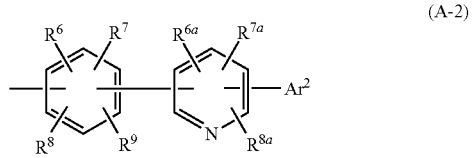

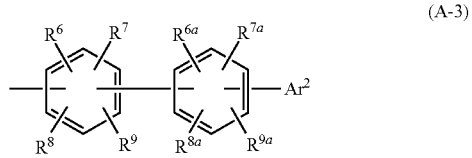

wherein R$^6$ to R$^9$ and Ar2 are as defined in said structural formula (1a).

7. Naphthotriazole derivatives according to claim 1, wherein in said general formula (1), Ar$^2$ is a pyridyl group in the structural formula (1a).

8. Naphthotriazole derivatives according to claim 1, wherein in said general formula (1), A is a monovalent group represented by any one of the following structural formula (A-4), (A-5), (A-6) or (A-7),

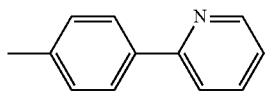 (A-4)

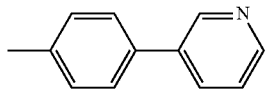 (A-5)

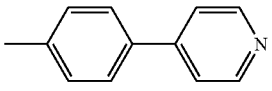 (A-6)

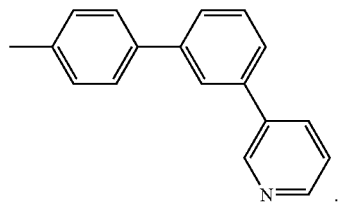 (A-7)

9. An organic electroluminescent device having a pair of electrodes and at least one organic layer interposed therebetween, wherein naphthotriazole derivatives of claim 1 are used as materials for constituting at least one organic layer.

10. The organic electroluminescent device according to claim 9, wherein said organic layer is an electron-transporting layer.

11. The organic electroluminescent device according to claim 9, wherein said organic layer is a hole-blocking layer.

12. The organic electroluminescent device according to claim 9, wherein said organic layer is a luminous layer.

13. The organic electroluminescent device according to claim 9, wherein said organic layer is an electron injection layer.

* * * * *